(12) United States Patent
Yepez, III et al.

(10) Patent No.: US 8,013,600 B1
(45) Date of Patent: Sep. 6, 2011

(54) MOUNTABLE EDDY CURRENT SENSOR FOR IN-SITU REMOTE DETECTION OF SURFACE AND SUB-SURFACE FATIGUE CRACKS

(75) Inventors: Esteban Yepez, III, Albuquerque, NM (US); Dennis P. Roach, Albuquerque, NM (US); Kirk A. Rackow, Albuquerque, NM (US); Waylon A. DeLong, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 630 days.

(21) Appl. No.: 12/119,009

(22) Filed: May 12, 2008

Related U.S. Application Data

(60) Provisional application No. 60/988,931, filed on Nov. 19, 2007.

(51) Int. Cl.
  *G01N 27/82* (2006.01)
(52) U.S. Cl. .......................................... 324/240
(58) Field of Classification Search ................... 324/240
  See application file for complete search history.

(56) References Cited

U.S. PATENT DOCUMENTS

| | | | |
|---|---|---|---|
| 4,706,020 A | 11/1987 | Viertl et al. | |
| 5,389,876 A | 2/1995 | Hedengren et al. | |
| 5,510,709 A * | 4/1996 | Hurley et al. | 324/242 |
| 6,037,768 A * | 3/2000 | Moulder et al. | 324/225 |
| 6,501,267 B1 * | 12/2002 | Kurokawa et al. | 324/242 |
| 7,098,655 B2 | 8/2006 | Yamada et al. | |
| 7,557,570 B2 * | 7/2009 | Crouch et al. | 324/229 |
| 7,560,920 B1 * | 7/2009 | Ouyang et al. | 324/242 |
| 2002/0163333 A1 * | 11/2002 | Schlicker et al. | 324/242 |
| 2003/0164700 A1 | 9/2003 | Goldfine et al. | |
| 2004/0189290 A1 * | 9/2004 | Lehman et al. | 324/230 |

OTHER PUBLICATIONS

J Fava, et al, Design and Construction fo Eddy Current Sensors with Rectangular Planar Coils, 16th WCNDT 2004—World Conference on NDT Aug. 30-Sep. 3, 2004—Montreal, Canada.

Vorgelegt Von, Eddy Current Displacement Sensor with LTCC Technology, Datum der Promotion: Mar. 22, 2005.

Nortec 500, Eddy current flaw detectors, http://www.olympushndt.com/en/500/.

Omniscan MX ECA, Eddy current Array Technology, http://www.olympusndt.com/en/omniscan-eca/.

Andrel Ptchelintsev, Two-dimensional finite element model for a long rectangular eddy current surface coil, 0034-6748/2000/71(2)/571/6, 2000 American Institute of Physics.

T Dogaru, et al, Deep Crack Detection Around Fastener Holes in Airplane Multi-Layered Structures Using GMR-Based Eddy Current Probes, CP700, Review of Quantitative Nondestructive Evaluation vol. 23, 2004 American Institute of Physics.

Neil Goldfine, et al, Surface Mounted and Scanning Periodic Field Eddy-Current Sensors for Structural Health Monitoring, 0-7803-7231-X/01/$10.00/2002 IEEE.

Vladimir Zilberstein, et al, Residual and Applied Stress Estimation from Directional Magnetic Permeability Measurements with MWM Sensors, Journal of Pressure Vessel Technology, Aug. 2002, vol. 124.

(Continued)

*Primary Examiner* — Huy Q Phan
*Assistant Examiner* — Joshua Benitez
(74) *Attorney, Agent, or Firm* — Olivia J. Tsai

(57) ABSTRACT

A wireless, integrated, mountable, portable, battery-operated, non-contact eddy current sensor that provides similar accuracy to 1970's laboratory scale equipment (e.g., a Hewlett-Packard GP4194A Impedance Analyzer) at a fraction of the size and cost.

33 Claims, 28 Drawing Sheets

OTHER PUBLICATIONS

Washabaugh, Andrew, et al., Shaped-Field Eddy-Current Sensors and Arrays, Smart Nondestructive Evaluation for Health Monitoring of Structural and Biological Systems, Tribikram Kundu, Editor, Proceedings of SPIE vol. 4702 (2002) 2002 SPIE-0277-786X/02/.

* cited by examiner

A = Sensor Response to Crack (flaw signal)
B = Sensor Response at Uncracked Region (signal noise)

EC Sensor Design Parameters

Deep Penetration of Magnetic Field for Subsurface Crack Detection in Coil Designed to Accommodate Max Lift-off (d) Expected

MOUNTABLE EDDY CURRENT SENSOR FOR IN-SITU REMOTE DETECTION OF SURFACE AND SUB-SURFACE FATIGUE CRACKS

CROSS-REFERENCE TO RELATED APPLICATIONS

This application claims priority to and the benefit of U.S. Provisional Patent application No. 60/988,931 filed Nov. 19, 2007, which is incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

BACKGROUND OF THE INVENTION

1. Field of the Invention (Technical Field)

The present invention relates to sensors and methods for non-destructive evaluation (NDE) of structures such as bridges, aircraft, building supports, etc.

2. Description of Related Art

Structural health monitoring (SHM) is a growing concern of the engineering community. This need is even more intense in the case of aging aerospace and civil structures, many of which are operating well beyond their initial design lives. An unavoidable by-product of a metallic structure's use is the development of crack, corrosion, and other flaws ("faults") that degrade the structure over time. Significant cost barriers to replace these structures have created an aging infrastructure. These economic realities, coupled with an explosion in infrastructure development and unexpected phenomena that have accelerated decay, have placed even greater demands for structural health monitoring. In addition to the growth in infrastructure, the effort and frequency of maintenance and surveillance also increases with age. As a result, the costs to manage our aging infrastructure are rising at an unexpected rate. For example, aircraft maintenance and repairs represent about a quarter of a commercial fleet's operating costs.

Therefore, it is imperative that methods and apparatuses be developed which can quickly and easily assess the integrity of the structure. The application of distributed sensor systems can reduce these costs by allowing condition-based maintenance practices to be substituted for the current time-based maintenance approach. In addition, innovative deployment methods must be devised to overcome a myriad of inspection impediments stemming from accessibility limitations, complex geometries, and the location and depth of hidden damage.

Prevention of unexpected flaw growth and structural failure could be improved if remotely-accessible, on-board health monitoring systems are used to continuously assess structural integrity. Such systems would be able to operate in the field for extended periods and detect incipient damage before catastrophic failures occurs. With detection capabilities, failure signatures and the corresponding driving factors can be extracted from the data. As a result, condition-based maintenance practices could be substituted for the current time-based maintenance approach.

A "Smart Structure" is one which is sufficiently instrumented so that the data can be synthesized to form an accurate real-time picture of the state of the structure in all its critical aspects. By positioning sensors around the critical regions of the structure (i.e., locations where fatigue cracks are most likely) it is possible to establish an in-situ sensor network for continuous, real-time structural health monitoring.

A useful aspect of a "Smart Structure" is the ability to provide subsurface fault detection, in particular for cracks. Such crack detection requires a sensor with penetrating (strong EMF, or other Non-Destructive Evaluation (NDE) methodology) capability, yet able to be placed on a thin Process Control Device (PCD) (low profile) for mounting. Furthermore, it must also be sensitive enough to detect small cracks through: (1) non-conducting lift-off impediments such as composite, plastic or other coatings, and (2) conducting layers such as steel or aluminum so that sub-layer cracks can be detected.

The present invention provides such a sensor, providing deep penetration with a strong enough magnetic field to interrogate thick, mutli-layer, conductive structures. It can also overcome the "lift-off" effects of nonconductive layers/coatings. Such lift-off effects lower the strength of the eddy current (EC) field in the area of interest, and so the coil design in this sensor, along with its mode of operation, is a critical aspect of the sensor's unique capabilities.

Other advantages of on-board distributed sensor systems are that they can eliminate costly, and potentially damaging, disassembly, improve sensitivity by producing optimum placement of sensors with minimized human factors concerns in data acquisition, and decrease maintenance costs by eliminating more time-consuming manual inspections.

Through the use of the sensor of the invention it is possible to quickly, routinely, and remotely monitor the integrity of a structure in service. It provides a reliable structural health monitoring system that can automatically process data, assess structural condition, and signal the need for human intervention. This sensor is able to detect incipient damage before catastrophic failures occur.

The replacement of present-day manual inspections with automatic health monitoring would substantially reduce the associated life-cycle costs. Another important item to note is that the ease of monitoring an entire network of distributed sensors means that structural health assessments can occur more often, allowing operators to be even more vigilant with respect to flaw onset. In addition, corrective repairs initiated by early detection of structural damage are more cost effective since they reduce the need for subsequent major repairs.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

A wireless, integrated, mountable, portable, battery-operated, non-contact eddy current sensor that provides similar accuracy to 1970's laboratory scale equipment (e.g., a Hewlett-Packard GP4194A Impedance Analyzer) at a fraction of the size and cost.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1A:
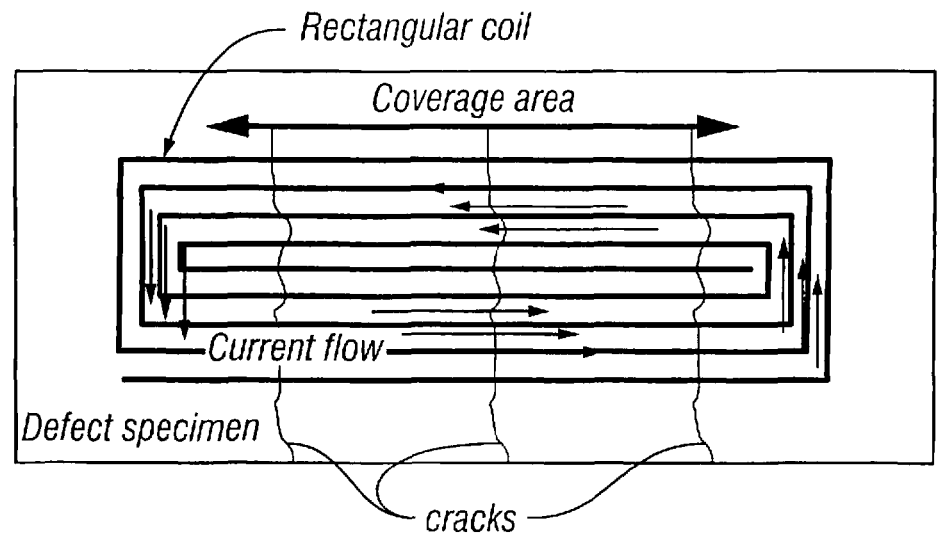
FIGS. 1(a)-(e) show example crack propagations and planar coil designs useful with the present invention.
Figure 1B:
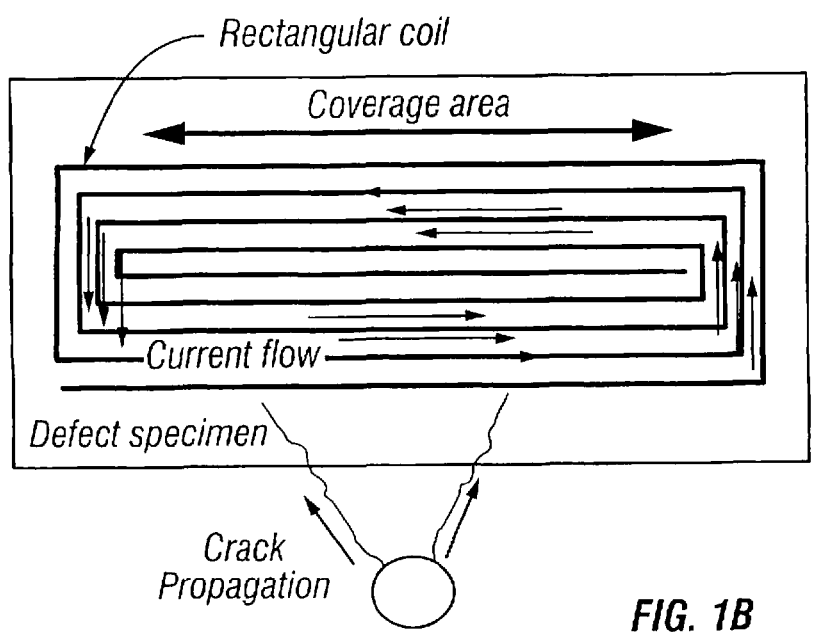
Figure 1E:
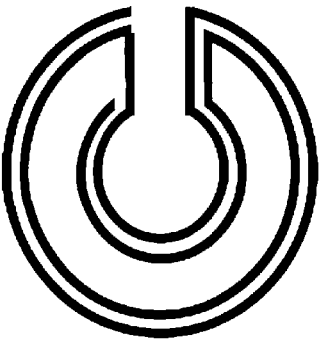

The present invention relates to a wireless, integrated, mountable, portable, battery-operated non-contact eddy current sensor that provides similar accuracy to 1970's laboratory scale equipment (e.g., a Hewlett-Packard GP4194A Impedance Analyzer) at a fraction of the size and cost. The invention preferably utilizes an Analog Devices AD5933 impedance analog-to-digital converter integrated circuit or equivalent custom hardware or mixture of customized off-the-shelf hardware (such as a combination of Direct Digital Synthesizer, Digital-to-Analog converter, Analog-to-Digital converter, operational amplifiers, and multiplexors) and custom software. The sensor is sensitive enough to detect faults (i.e., cracks, defects) with a lift-off distance greater than at least 500 mils. A directly integrated planar coil provides consistency in coil characteristics. The sensor can operate from at least 1 kHz to 100 kHz, permitting a battery of calibration and measurement techniques. The device contains a micro-controller and high precision components to permit calibration and measure small changes in inductance.

Low-power, 2.4 GHz or other wireless access provides remote communication, and local non-volatile memory can store weeks of measurements between data retrieval sessions. The size, weight, and power consumption of the device allow it to be mounted directly to the structure and to operate for extensive periods without external intervention. The device reduces the number of visits to the structure to retrieve data from the device. The small size and low cost of the device allow the user to employ several devices to monitor several parts of a structure. The incorporation of ZigBee wireless protocol enables the devices to work in a self-configurable, self-healing sensor network that can be combined with off-the-shelf products to provide range extension and multiple communications options. A range extender can be used to extend the range of the system to a radius of 5 miles. In cases where cellular coverage is present, it may be desirable to use a cellular OEM module to communicate via the cellular network.

The measurement device of the invention preferably comprises a direct digital synthesizer to generate the signal for the eddy current sensor and to synchronize the digital-to-analog and analog-to-digital converters to measure impedance changes. A microcontroller, or equivalent device, is used to calculate the complex impedance of the sensor. The complex impedance can be determined by using the Discrete Fourier Transform to measure the magnitude and phase response of the sensor. The magnitude and phase can then be used to calculate the resistive and reactive impedance components of the sensor. A preferred device configuration incorporates a Freescale MC13124 micro-controller integrated with 2.4 GHz wireless communications capability; an Analog Devices AD5933 impedance IC; and high precision components to permit: calibration, drive an eddy current sensor, and measure small changes in inductance.

Other embodiments of the invention can also be developed using other microcontrollers, digital signal processors, field programmable arrays and application-specific integrated circuits. It can contain separate ICs to perform the necessary operations to drive the sensors, configure the detection hardware, compute a complex impedance value for a particular frequency of operation, store the information, and send the information to an external device for observation and/or additional processing.

Figure 10:
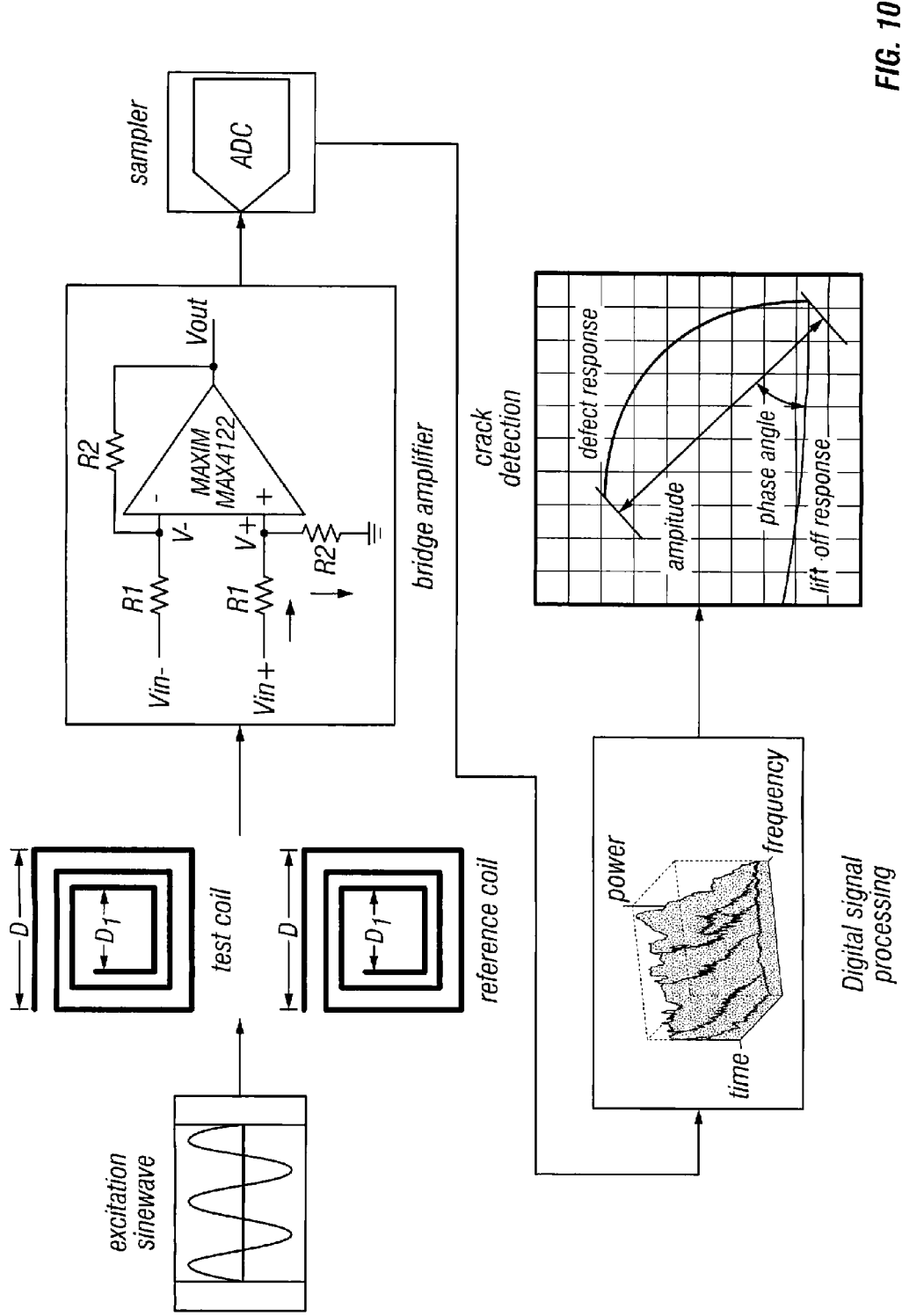
FIG. 10 illustrates a preferred method of the invention for processing data received remotely a sensor of the invention.

In one mode, the system generates an excitation waveform to drive a pair of reference and test coils, uses detection circuitry to amplify the differential response, digitizes the analog waveform, and performs frequency-based transformations to generate a complex response that can be compared temporally and communicated to a remote device that can plot the response (see FIG. 10). Local non-volatile memory can store weeks or months of measurements between data retrieval sessions. In addition, software can filter locally stored measurement data and apply compensation to improve sensitivity and identify significant events. The employment of localized heuristics allows the device to identify significant events and adjust its sampling rates to correspond to event frequency. A real-time-clock (RTC) automatically wakes up the device to control the intervals for measurement and device self-tests. This automatic operation permits real-time, in-situ structural health monitoring so that flaw onset can be detected essentially immediately. The RTC also conserves battery life by placing the device in an ultra-low power mode when it is not making measurements, performing self-tests, communicating, or performing other activities.

The device can adjust the drive frequency of the sensor coil(s) to penetrate conductive materials or to determine the depth of a flaw. Scalable scanning frequencies are preferably employed to gauge depth of damage and overcome conductive displacement. Lower frequencies provide deeper penetration into conductive materials and therefore can determine the depth of a flaw, while higher frequencies provide greater resolution of surface flaws. Together, scanning across multiple frequencies can provide additional information about the flaw's severity and trends.

The device can use programmable gain operational amplifiers to attenuate or amplify the output and input signals independently. A larger output signal can be used to increase the magnetic field and generate larger eddy currents inside of the specimen. A larger input signal can be used to maximize the dynamic range of the analog-to-digital converter and improve the signal-to-noise ratio.

The device can support multiple EC coils. This allows for differential mode of operation so that the sensor is self-nulling (no need for another sensor in an adjacent, unflawed area to produce a comparative signal) or allows the user to inspect these areas individually and thereby expand the coverage area. The measured impedance of each coil can be compared to itself over time or can be compared against the other coils to determine if a flaw is present.

The device preferably comprises a high pass filter of the measurement data to remove diurnal or other slowly-varying measurement changes. Filtering out these undesired events improves the sensitivity of the device. Crack onset will generate a non-linear change in measured impedance over time and the change will increase with varying degrees of acceleration as the crack grows. The cut-off frequency is user selectable. The device preferably also comprises a low-pass filter to remove high frequency vibrations and other artifacts that do not contribute to flaw detection. The cut-off frequency is again user selectable.

The device can operate from batteries for at least a full year. As the batteries deplete, the device can determine its discharge rate during operation and adjust its measurement interval to maintain a desired period of performance between battery recharges.

The use of thin, planar EC coils also provides the possibility to directly integrate the coils with the rest of the device so that wires are eliminated. This approach drives cost down by reducing part count. It also provides better SNR (Signal to Noise Ratio) because the resistive and reactive losses from the wires are eliminated.

The invention preferably uses large coils and low frequency for deep penetration to provide subsurface crack detection and/or overcome inspection impediments stemming from lift-off (non-conductive) surface coatings. Coils are preferably placed on a thin printed circuit board or flexible, non-conducting substrate (e.g., plastic, ceramic, polyamide) to produce a mountable (leave-in-place) sensor for field use.

In-situ SHM allows for real-time health monitoring so that flaw onset can be detected immediately. In-situ SHM also allows condition-based maintenance practices to be substituted for the current time-based maintenance approach. The mountable sensor of the invention produces uniform deployment (vs. hand-held human deployment). This produces a uniform response for more reliable and repeatable data. A hand-held NDI probe can result in varying signals depending on how well the person is able to maintain the orientation of the probe during the inspection. Hand deployment of EC probes results in a "wobble" issue where there is a signal change produced by unsteady application of a hand-held probe. This mounted sensor eliminates this additional "noise" resulting in more reliable inspections.

A large coil further allows for crack detection over a large area which is essential when monitoring regions which may have a widely varying crack propagation direction. The sensor can be customized in various shapes to monitor crack growth in different applications. It further provides the ability to adjust frequency to optimize signal as well as multiple modes of operation; a two-coil design allows for differential mode of operation so that the sensor is self-nulling (no need for another sensor in an adjacent, unflawed area to produce a comparative signal).

The use of a rectangular planar coil as shown in FIGS. 1(*a*) and (*b*), coupled with embedded processing, conditioning electronics, and wireless communications, provides a stand-alone solution to perform laboratory quality, remote, in-situ, real-time, non-contact, structural health monitoring. Planar coils provide a large coverage area. A single coil, or a matrix of coils, can be used to detect flaws over a large area, which is essential when monitoring regions which may have a widely varying crack propagation direction. A large radius coil is also required to overcome lift-off when the sensor can not be in direct contact with the underlying structure. As shown, cracks can either grow linearly or emanate radially. Since it is not possible to know how the crack will develop, a large coverage area is preferred to capture the crack as it propagates throughout the structure.

Figure 17:
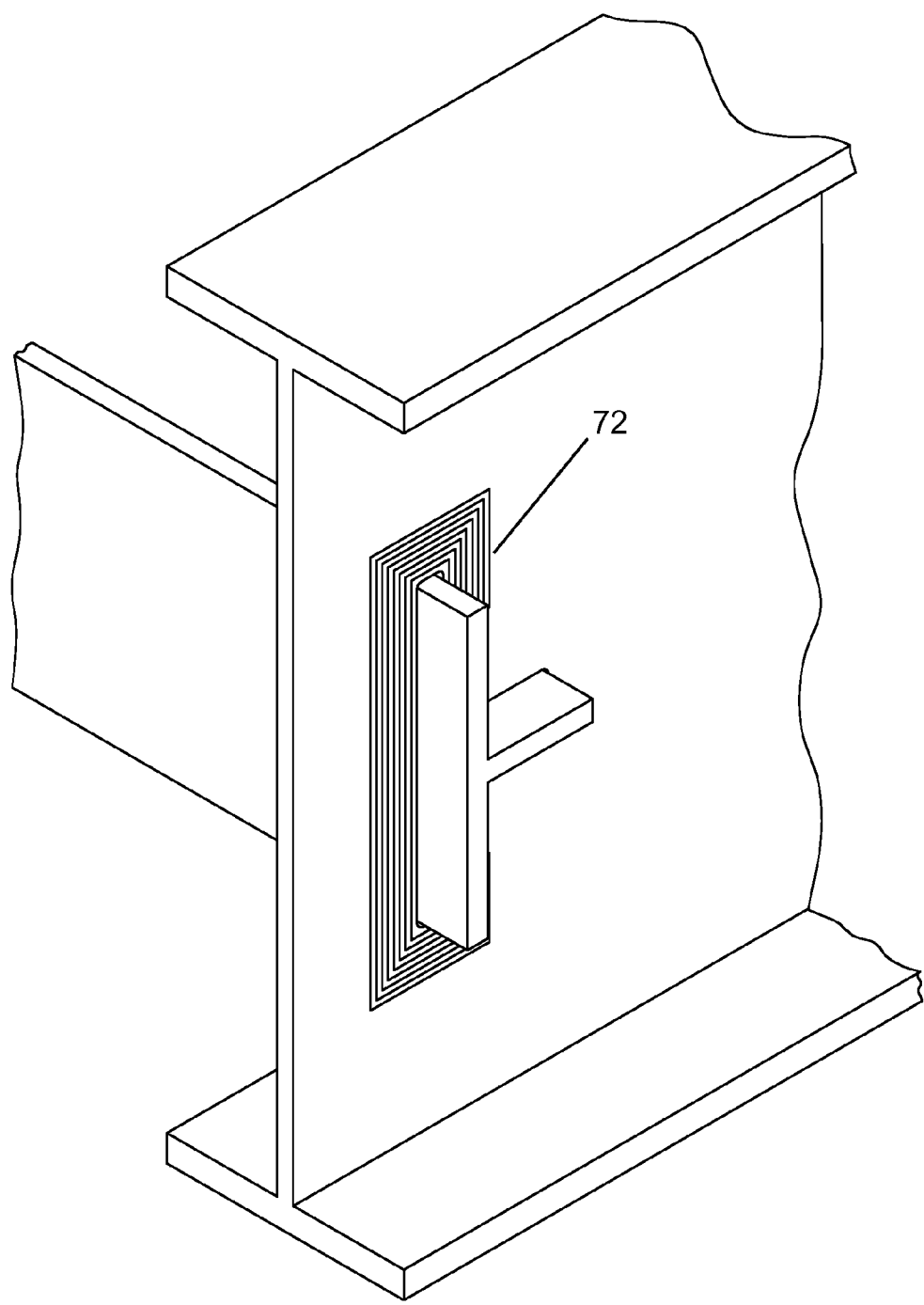
FIG. 17 shows a customized rectangular coil for beam joint inspection.
Figure 18:
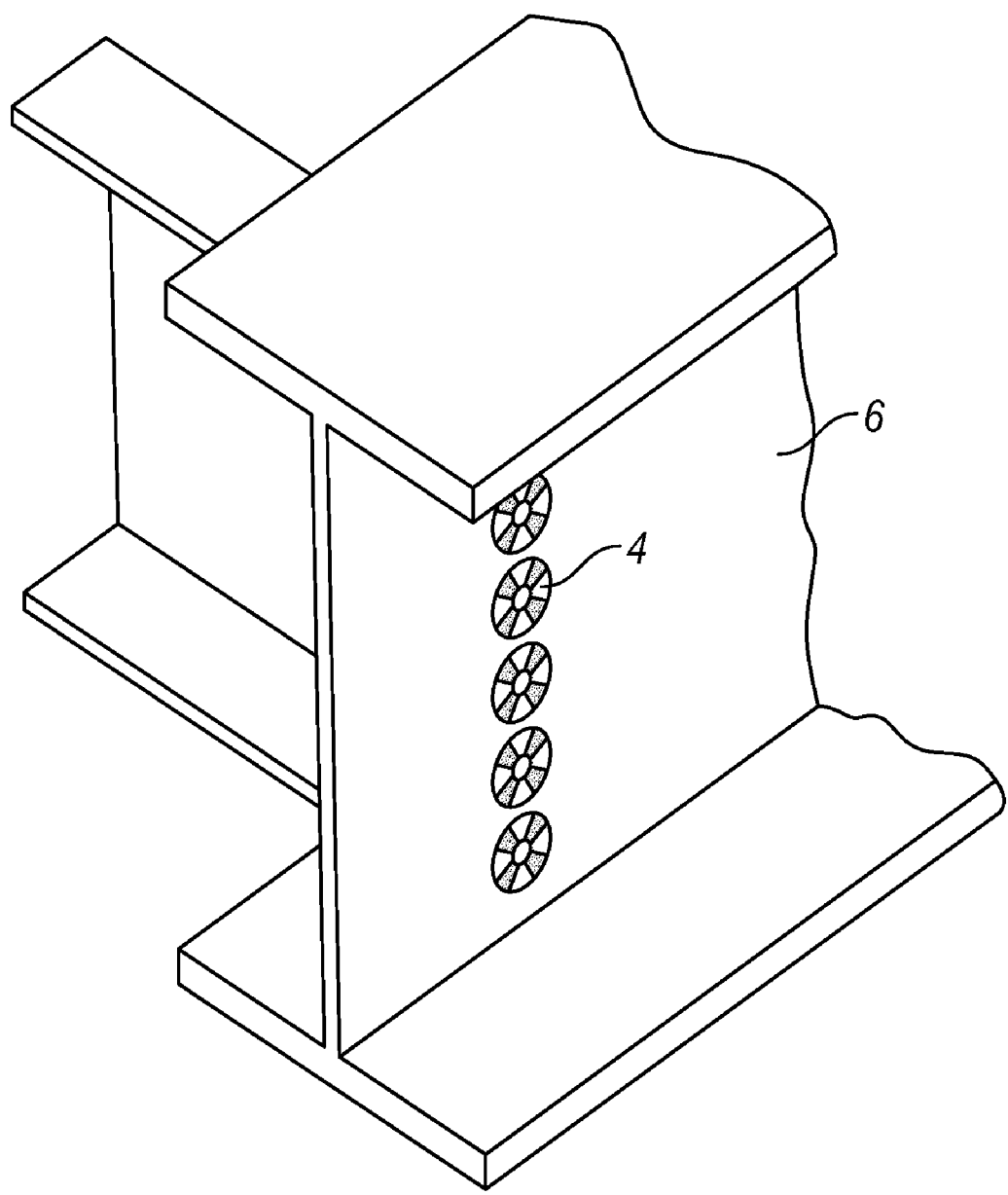
FIG. 18 shows a sensor array configuration for beam joint inspection.

Custom coverage coils can be configured to provide a specific coverage area while conforming to the structural dimensions. This flexibility can be useful in applications where the structure dimensions prohibit a rectangular form factor or where the crack growth characteristic is deterministic, or where there is a desired inspection area. FIGS. 1(*c*), (*d*), and (*e*) illustrate some useful planar coil designs. FIG. 17 illustrates a customized rectangular coil shape for beam joint inspection. This modified rectangular coil, 72, is preferably designed to monitor the entire perimeter of a beam joint by wrapping the coil along the edges at the intersection of the two structures. Customized coils are preferably produced for any custom shape needed for EC sensors. In addition to the customized rectangular coil for beam joint inspection illustrated in FIG. 17, a sensor array configuration as shown in FIG. 18 can be alternatively used for beam joint inspection. In FIG. 18, a sensor array monitors the opposite side of a beam interface. The sensor array is multiplexed to determine impedance changes among adjacent sensors, or against a designated reference sensor, to determine relative position of the incipient damage. The sensor array comprises a plurality of EC sensors 4 and sensor monitoring and data logging transmission electronics package 6.

A multi-coil configuration can also be employed for spatial and temporal resolution. Coils can be cascaded linearly (FIG. 2(*b*)), logarithmically, or in a matrix (FIG. 2(*a*)). This multi-coil information can be used to identify the location of a flaw or monitor how the flaw grows.

Figure 14:
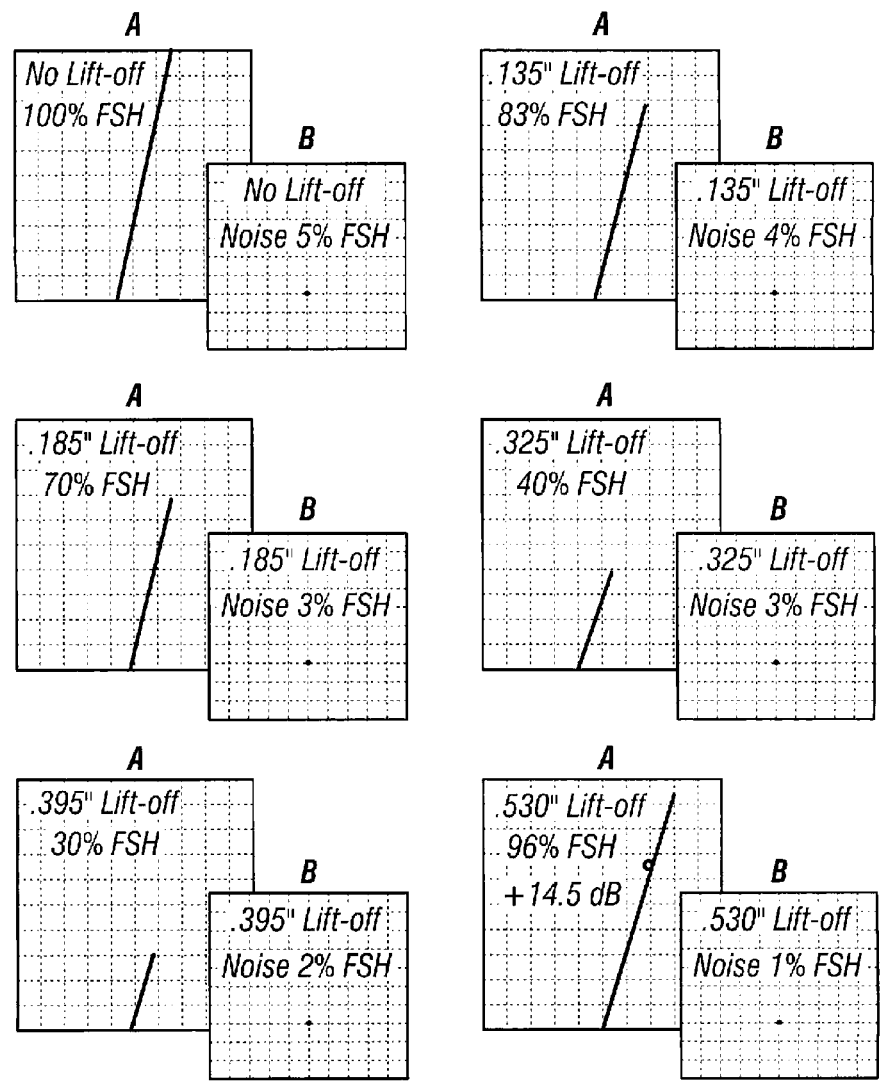
FIG. 14 shows crack detection performance of the invention for lift-off layers up to 0.530" thick.
Figure 15:
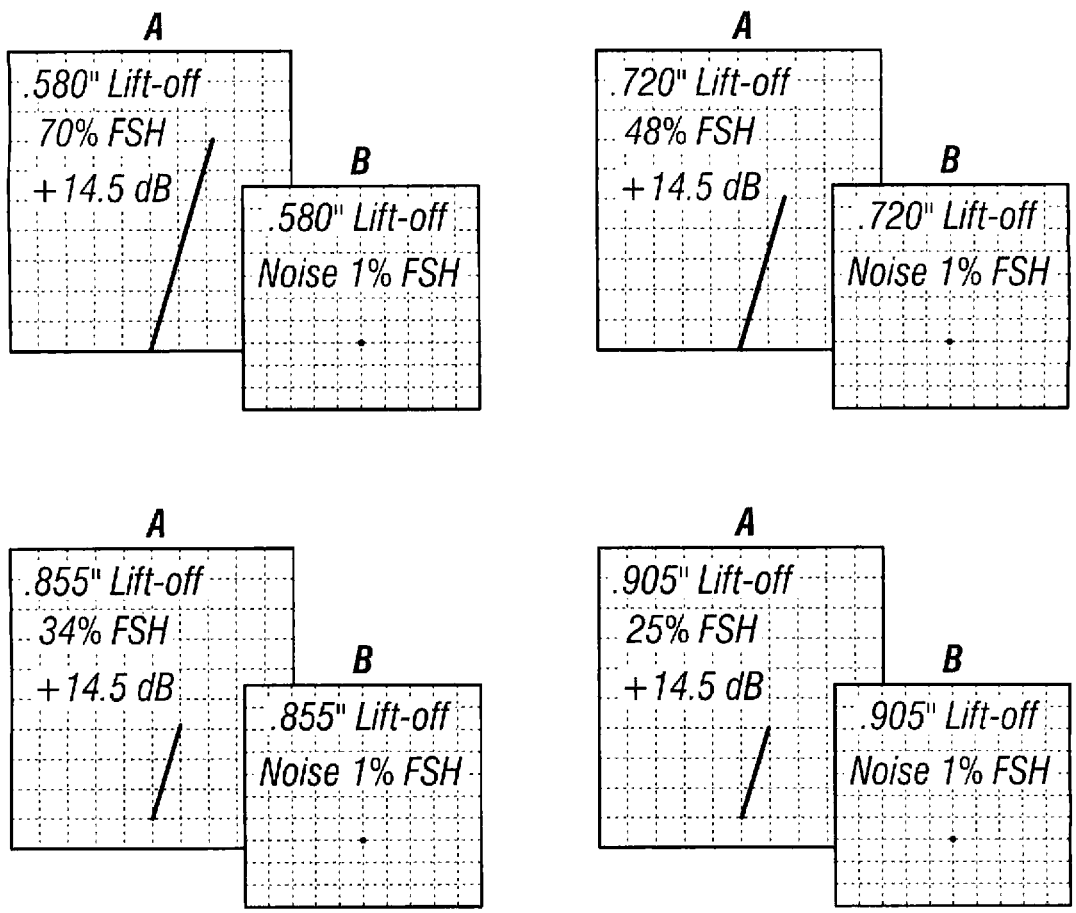
FIG. 15 shows crack detection performance of the invention for lift-off layers up to 0.905" thick.

Unlike ultrasonics that rely on strong adhesion and coupling with the device under test, eddy current sensing can tolerate weak adhesion and lift-off with the structure. As shown in FIGS. 14-15, the coil of the invention will respond to changes in lift-off, but it is largely sensitive to cracks. When the sensor is mounted to a underlying structure, its lift-off response in the x-axis will not change. However as a crack forms under the coil, the signal will grow vertically and can be detected very close to the lift-off crack apex.

The mounted sensing solution of the present invention will not experience fluctuations introduced from wobble in the sensor as it scans over a specimen. In manual inspections, wobble can be introduced by scanning over uneven surfaces, the application of different levels of pressure, or changes in the orientation of the sensor. The lift-off crack apex would be less certain under manual inspection because the "wobble" effect would generate a region of uncertainty around the apex. The result is that the crack would need to grow beyond the region of uncertainty before it could be detected. A tighter region of uncertainty promotes greater sensitivity than manual inspections because mounted sensors do not exhibit the larger region of uncertainty generated by the "wobble" noise of a manual scan.

Scalable scanning frequencies are preferably employed to gauge depth of damage and overcome conductive displacement. Lower frequencies provide deeper penetration into conductive materials and therefore can determine the depth of a flaw and higher frequencies provide greater resolution of surface flaws. Together, scanning frequencies can provide additional information about the flaw's severity and trends.

Temperature compensation can be employed to eliminate indirect deviation. The impedances of the structure and components will change with temperature. By calibrating the system to known quantities and correlating them against temperature, one can cancel out these effects and provide greater resolution. Furthermore, through self-calibration one can compensate for any drift and offsets in measurements to provide greater accuracy.

Data storage is preferably employed to enable filtering of historical data. Providing local storage allows the device to operate independently for long intervals between data uploads. In addition, software can filter historical information and apply compensation to improve sensitivity and identify significant events. The employment of power-saving modes and localized heuristics allow the device to identify significant events and adjust its sampling rates to correspond to event frequency.

Embodiments of invention preferably comprise co-located signal conditioning electronics. By placing the electronics close to the sensor coils, it is possible to minimize the noise introduced by long wires and obtain the best signal-to-noise ratios (SNRs) into the analog to digital converters.

The system of the invention preferably can be configured in, for example, at least two modes of operation: (1) a detection mode that employs a LC tank circuit that can detect a frequency shift in the resonant frequency of the LC circuit; and (2) an auto-balancing bridge mode that can measure changes in the coil's complex impedance to characterize the flaw.

By mounting the sensors directly it is possible to continuously monitor a structure and determine when a flaw occurs and monitor its growth and direction. From this information, one can determine the stresses experienced and determine how to best repair the structure.

As background, EC sensors use the principles of electromagnetic induction to identify or differentiate structural conditions in conductive metals. The presence of a crack is indicated by changes in the flow of eddy currents in the skin. When EC inspections are performed, an electrically conductive material is exposed to an alternating magnetic field that is generated by a coil of wire carrying an alternating current. As a result, eddy currents are induced on and below the surface of the material. These eddy currents, in turn, generate their own magnetic field, which opposes the magnetic field of the test coil. Cracks or thickness changes in the structure under inspection influence the flow of eddy currents and change the impedance of the test coil accordingly.

The presence of a crack is indicated by changes in the flow of eddy currents in the skin. EC signals are physically monitored using impedance-plane plots which show the reactive and resistive components of a coil as functions of frequency, conductivity, or permeability. EC instruments record these impedance changes and display them in impedance plane plots to aid the flaw detection process.

Figure 3:
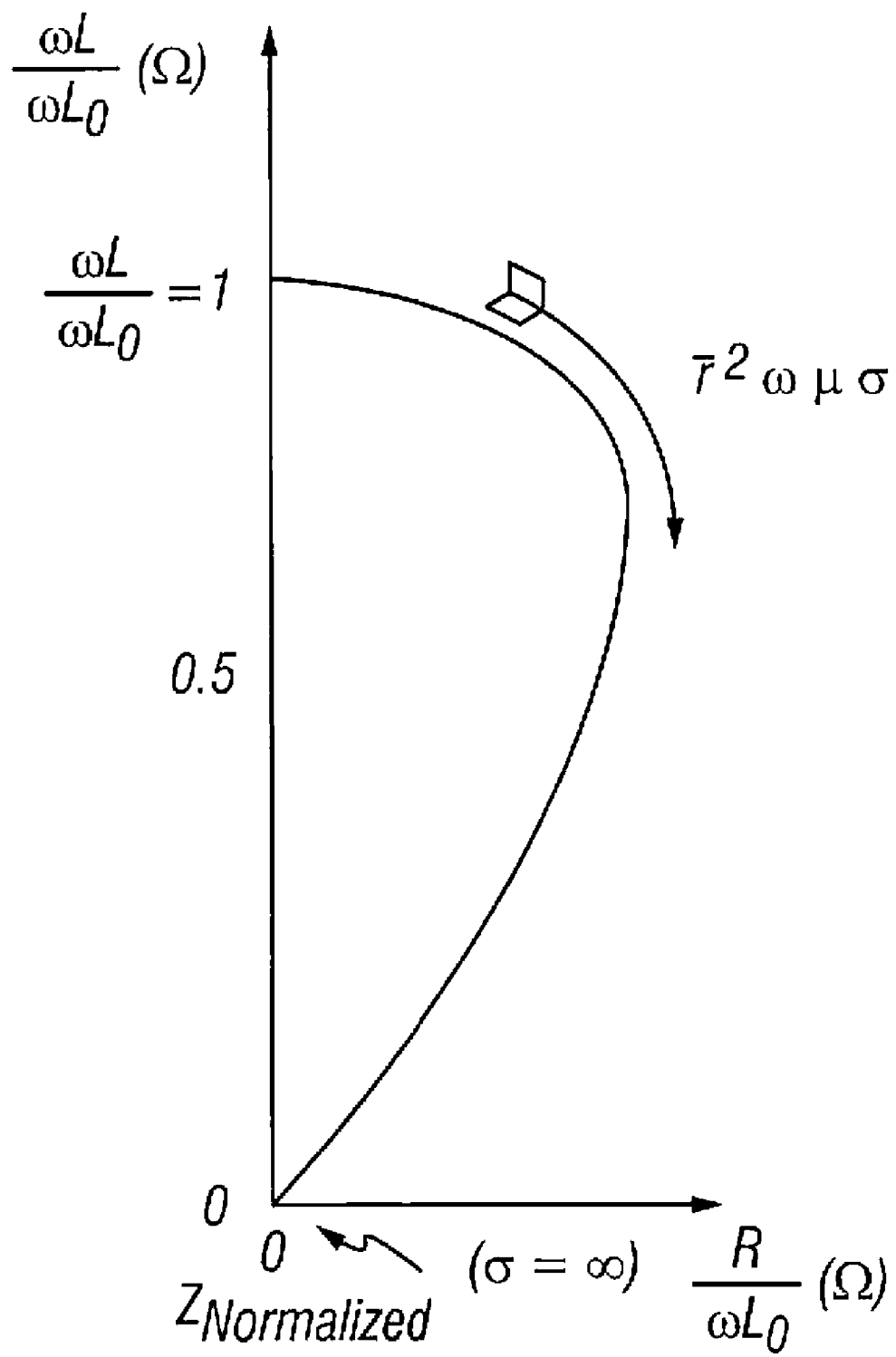
FIG. 3 is a graph of the normalized impedance plane plotted using the characteristic length parameter.

When working with eddy currents, impedance plane plots provide useful insight to the operation of the sensor. Referencing FIG. 3, the impedance of the coil is a complex number: it contains a real, or resistive component that represents the energy lost as heat in the structure (x-axis), and an imaginary, or reactive component that represents the energy storage of the coil (y-axis). To normalize the data, firstly the resistance at infinite lift-off is subtracted from the resistive component, and secondly, both the resistive and reactive components are divided by the reactive component. This generates a curve that starts at a purely reactive response at infinite lift-off, experiences a resistive affect as the coil moves closer to the structure and terminates at the origin where the induced eddy currents completely cancel out the currents in the coil. The resistive component first grows as energy is lost to heat, but then drops off as the majority of energy is transferred directly into the structure.

The response of the coil can also be normalized by the coil radius, the frequency of operation, and the conductivity and permeability of the structure. These normalizations permit objective comparison of various techniques. Again referring to FIG. 3, it is illustrated that the response of the coil moves from the upper left, along the curve, and towards the origin as a function of these factors. Hence a user can adjust the operating point of a sensor by adjusting one of these many parameters.

The depth of penetration of eddy currents is inversely proportional to the product of magnetic permeability, electrical conductivity, and frequency of the inducing currents. High frequency eddy current (HFEC) currents above 100 kHz are most sensitive to discontinuities on the surface next to the coil and are used to detect near-surface flaws. Low frequency eddy current (LFEC) ranging from 100 Hz to 10 kHz are used to penetrate the structure to detect flaws deep within underlying structure. By measuring the phase, it is possible to determine the depth of the defect.

An impedance plane display showing phase and amplitudes of EC signals generated by cracks of varying depths illustrates a rotated response so that the lift-off axis is oriented horizontally rather than vertically. Also the inspector will preferably amplify the response and place the apex of the operating region in the lower right-hand corner. This operating region represents a point along the curve in FIG. 3. Magnitude and phase response of the coil behave in an understood manner with increasing depth.

Figure 4:
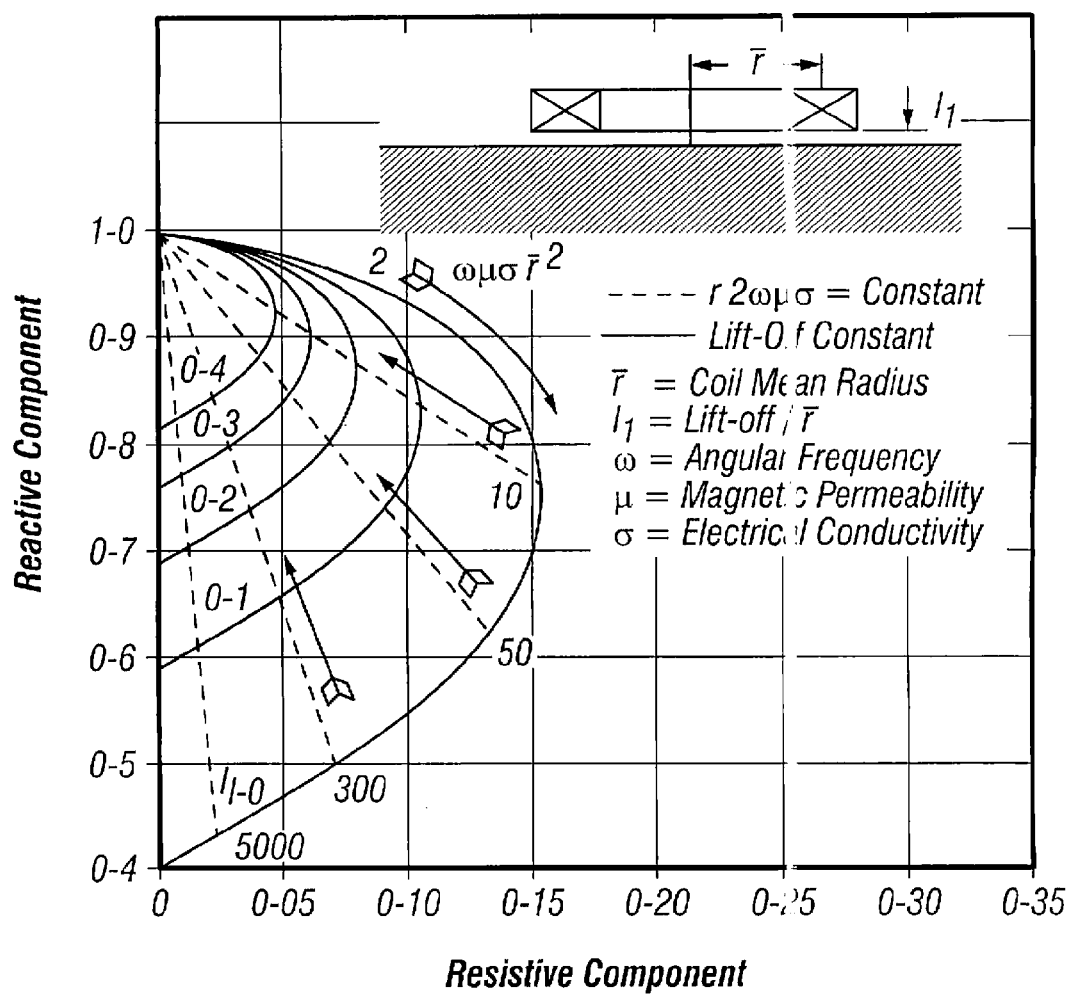
FIG. 4 illustrates lift-off impact on impedance plane plots.

The lift-off, or the distance between the sensor and the structure, also impacts the sensitivity of the EC sensor. A gap introduced by air, or any non-conductive medium, decreases the coupling ratio between the coil and the structure. Eventually, the displacement becomes large enough that the coil can no longer "sense" the structure. The graph in FIG. 4 brings this point home. The user operates on the outermost curve when in direct contact with the structure. As lift-off increases, the curve moves closer to the upper left corner of the graph, representing no object present. It is desirable to operate in the outermost curves to obtain the best sensitivity to impedance changes. As a side bar, FIG. 4 illustrates the lift-off curves that converge on the normalized infinite lift-off point of (0,1). It is this curve that inspectors rotate so that it is oriented along the x-axis. This rotation is done so that the user can maximize the sensitivity of the sensor in the y-axis where a crack response will be drawn, while minimizing the lift-off and wobble effects that occur in the x-axis.

Figure 5:
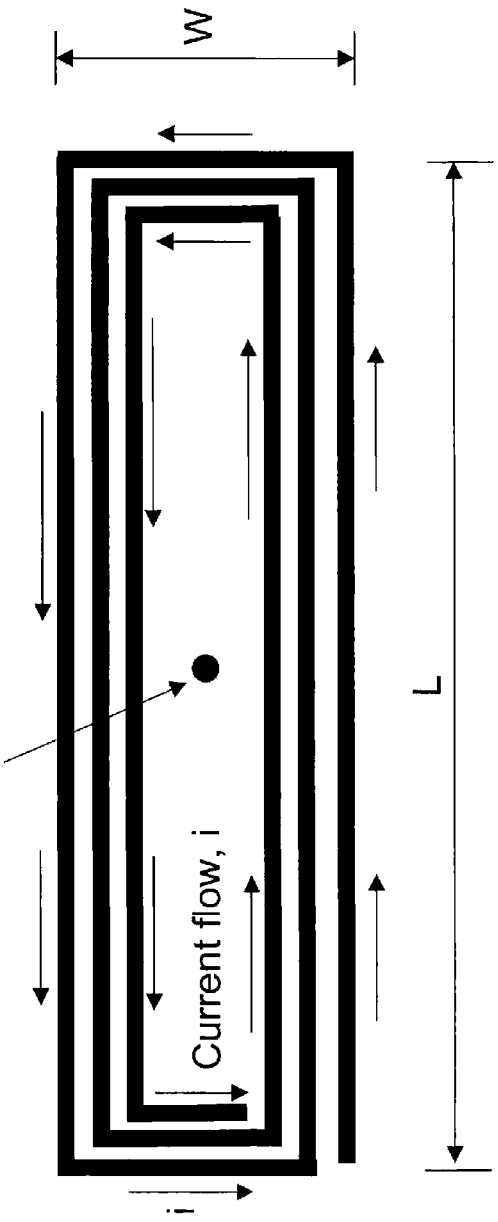
FIG. 5 illustrates magnetic field strength for rectangular coils.

When mounted, the EC sensor of the invention is capable of inspecting a large area because the user can only estimate, not pin-point, the location and path of incipient cracks. The eddy current coil of the invention is preferably designed in a rectangular form factor to provide uni-axial crack detection. FIG. 1(a) demonstrates how the length of the coil is oriented in parallel to the strain axis of the structure so that cracks will have the opportunity to intercept the coil and alter the eddy currents in the material directly below the coil. This orientation maximizes detection length, while restricting the coil's width to limiting the overall integration area. Additionally, the rectangular structure can also be used to detect cracks that grow radially from a particular stress point in the structure (see FIG. 1(b)). More importantly, since the length of the coil dominates the width of the coil, the magnetic field density along the lengthwise axis of the coil becomes a function of the coil's width. Hence a uniform magnetic field is developed among most of the coil's length (see FIG. 5) that can be approximated by a pair of infinite wires with currents flowing in opposite directions.

A planar coil can use FR4, Kapton, and other thin, polymeric films as a flexible insulating substrate to permit the deployment of inexpensive custom coil designs that optimize crack detection in a structure over a large region of interest without the need for direct contact with the structure. Custom-wound air core or ferrite core coil designs would be expensive. The alternative of interconnecting several of these large pancake coils to span the same coverage area of a single planar rectangular coil on thin film would be expensive and require individual compensation since each custom wound coil would exhibit different impedance characteristics.

Planar coil designs using modern PCB (Printed Circuit Board) and flexible thin film fabrication techniques permit the deployment of inexpensive, custom coil designs that optimize crack detection in a structure over a large region of interest, without the need for direct contact with the structure. The coil can be modified to support larger lift-off distances. In circumstances where it is possible to predict the strain vectors and estimate the likely regions for crack initiation and growth, custom planar coil designs are best suited because they can "enclose" the region and provide earlier detection. The length of the coil does not need to be straight, and can be aligned to follow the strain axis to increase the coverage area and maximize crack detection. For example, a U-shaped coil (FIG. 1-C) may provide better coverage than a rectangular coil for certain faults. Another alternative configuration would be a serpentine coil layout, criss-crossing a known crack several times.

Figure 16A:
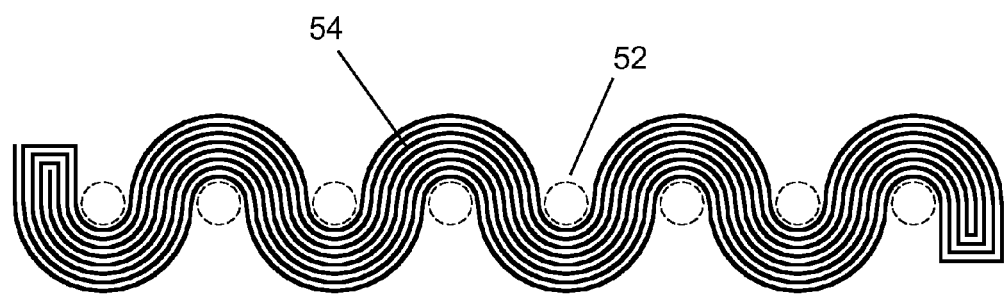
FIGS. 16A-D show serpentine coil designs to examine fasteners for longitudinal cracks.
Figure 16B:
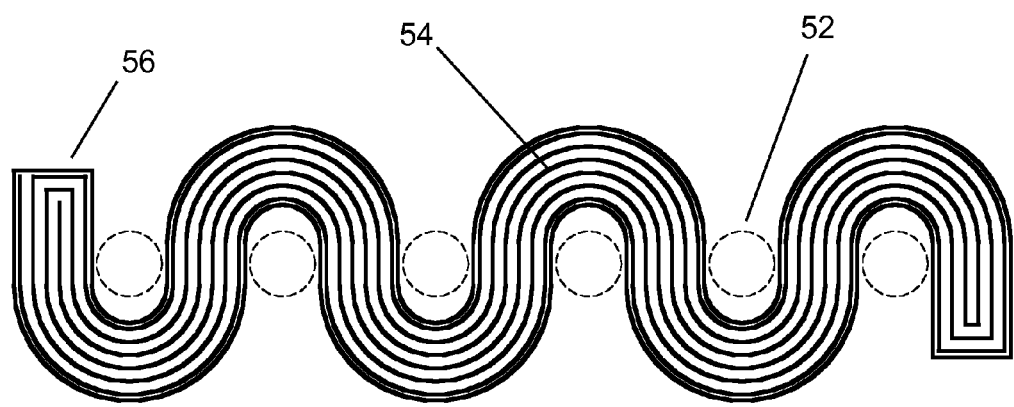
Figure 16C:
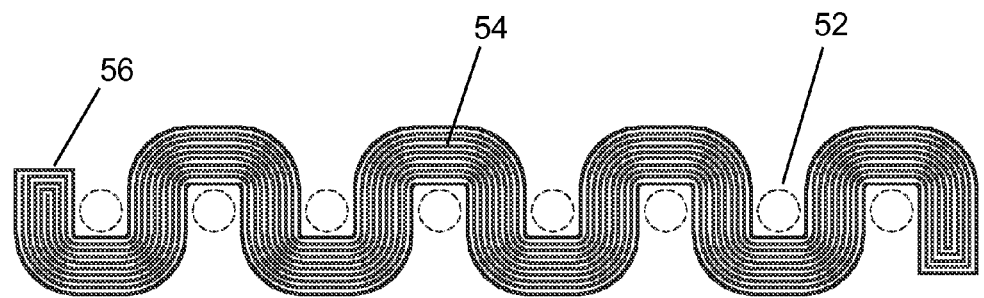
Figure 16D:
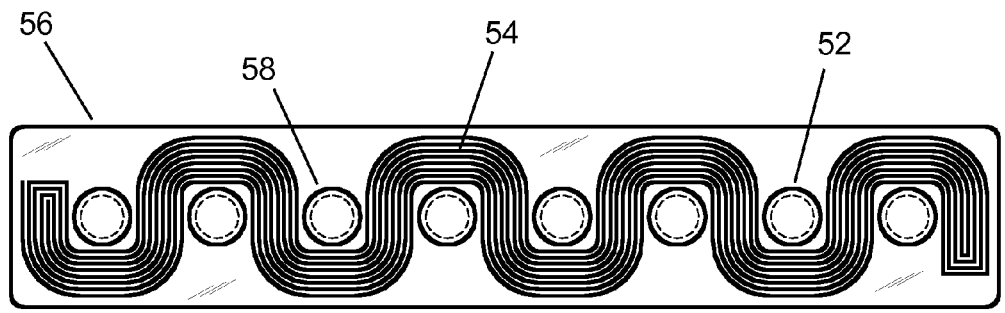

Serpentine coil design examples are shown in FIGS. 16A-D. This serpentine configuration is preferably used to examine a row of evenly-spaced fasteners (e.g., rivets). These meandering, serpentine coil design examples comprise fastener, hole, or other crack initiation site 52, and serpentine-shaped sensor coil layout 54. The electrical traces of coil 54 are fabricated on top of a thin, flexible, insulating substrate 56. In FIGS. 16B and 16C, substrate 56 conforms to and closely matches the outer shape of serpentine coil 54. In FIG. 16D, substrate 56 is rectangular shaped and has cutouts 58 that register and fit closely around holes 54. As illustrated by FIGS. 16A-D, there are a variety of ways to implement the serpentine design to achieve good coverage, while still considering the manufacturing aspects of coil design. For example, coil densities and coil sizes can vary.

Figure 1D:
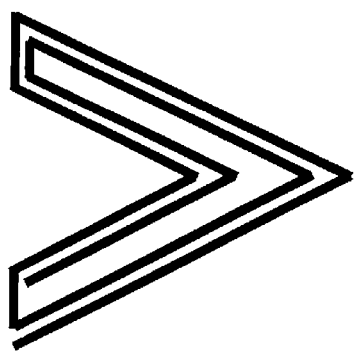
Figure 1C:
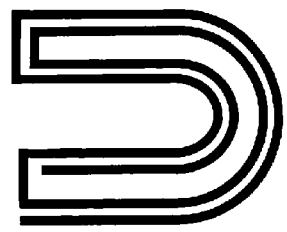
Figure 2B:
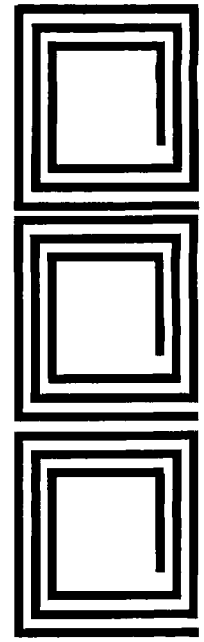
FIG. 2 show example matrix and cascade configuration of multiple coils.
Figure 2A:
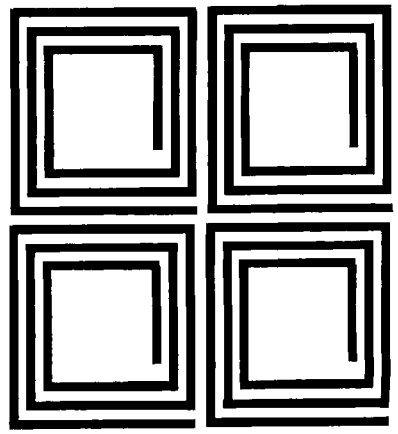

In addition to the U-Shape, a V- or C-shaped coil may be desired (see FIGS. 1(d) and (e)). Another possibility is to employ concentric coils to observe the rate of crack growth. In any case, these designs can be developed quickly and inexpensively with Computer-aided design (CAD) software and reproduced within 24-hours on a printed circuit board with consistent characteristics. Additionally, a thin film solution could employ a serious of sectors or concentric regions for detection to track the growth of a crack (see FIGS. 2(a) and (b)). The benefit of this approach is that the user can determine the starting point of the crack and monitor its growth. A quadrature coil configuration (FIG. 2(a)) could be used to determine the region where a crack started. FIG. 2(b) illustrates a cascaded coil design that can be used to monitor a crack as it grows from left to right. Furthermore a combination of a rectangular coil followed by separate square coils could be employed to first detect the crack and then determine the position where it penetrated the rectangular coil. A third row of offset square coils could be used to determine the orientation of the crack.

Often the structures of interest are not directly accessible; they might be covered with protection layers (e.g., foam, rubber, coatings, etc.) or strengthened by another structure (a conductive plate or composite panel). To be a useful SHM component, the EC sensor must penetrate either/both non-conductive or conductive gaps between the planar coils and the structure. Fortunately, since eddy currents are created using an electromagnetic induction technique, the inspection method does not require direct electrical contact with the underlying structure. Although non-conductive materials placed between the EC coil and the structure do not alter the magnetic fields, the field degrades as the lift-off (i.e., separation) distance increases; it is the weakened magnetic field that penetrates the structure's surface and generates the eddy currents used for crack detection.

Figure 6:
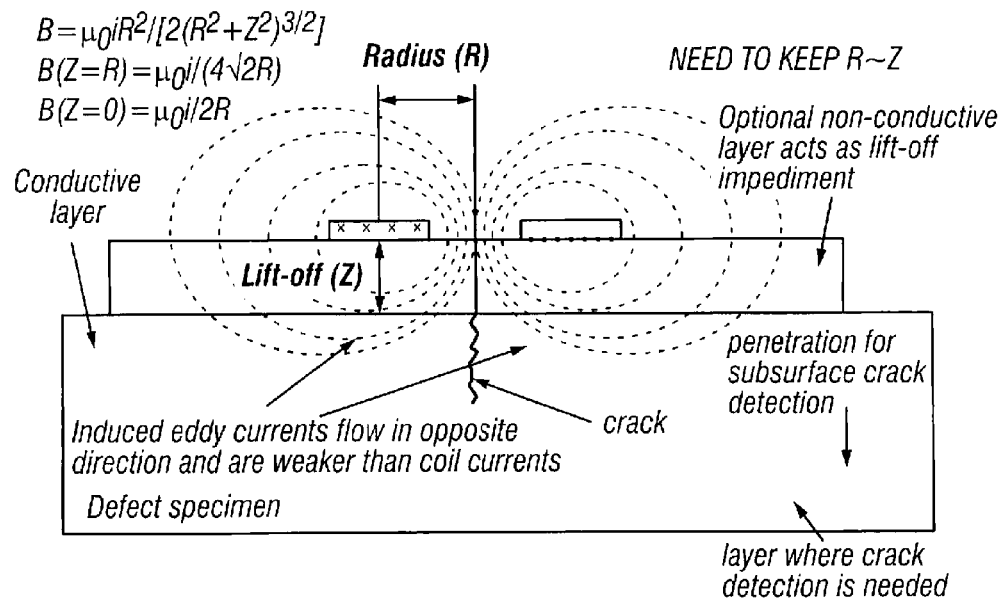
FIG. 6 illustrates magnetic flux density as a function of displacement, Z, for non-conductive gaps.

As depicted in FIG. 6, the density of the magnetic fields is determined by the magnetic flux of the coil. The field strength drops off by the cube of the distance from the coil. The way to expand the coil's range is to increase the radius so that it offsets the displacement. By setting the displacement equal to the coil radius, the magnetic field strength falls off linearly with the radius.

$$B = \frac{\mu_0 i R^2}{2(R^2 + Z^2)^{\frac{3}{2}}}, B(R = Z) = \frac{\mu_0 i}{4\sqrt{2}\,R} \qquad \text{(eq. 1)}$$

Figure 7:
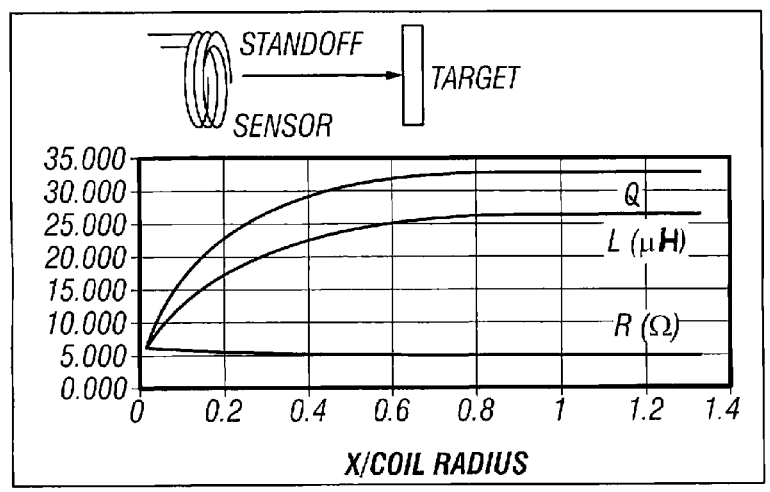
FIG. 7 illustrates proximity as a function of radius.

Using the above equation, it follows that the coil's sensitivity is essentially flat beyond 1× the radius. Ideally, the coil should be designed with a radius set to 2× the displacement, although aggressive designs can use 1×. FIG. 7 illustrates how the resistance, inductance and Q of the coil change with proximity. In the graph, the proximity is normalized by the coil radius (x-axis), and the response (y-axis) is in units (L in μH, R in ohms, Q in units). This phenomenon can also be illustrated using the normalized impedance curves in FIG. 4 that show how the sensor response drifts from the operating point on the outer curve towards the (0,1) origin, with increasing lift-off. Again, a rectangular design that sets the width to roughly correspond to the lift-off distance de-couples the "range" of the coil from its ability to detect a crack in the structure.

Figure 23:
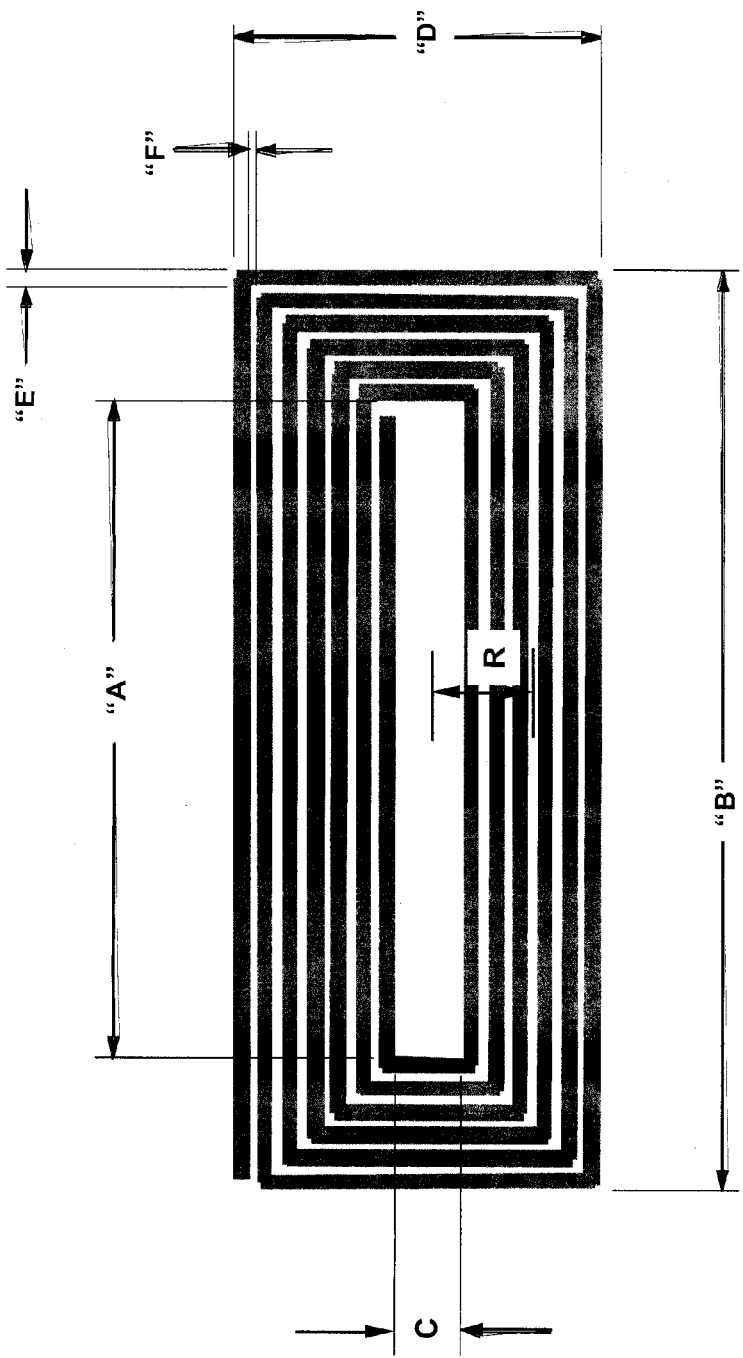
FIG. 23 shows a rectangular EC planar coil design.
Figure 24:
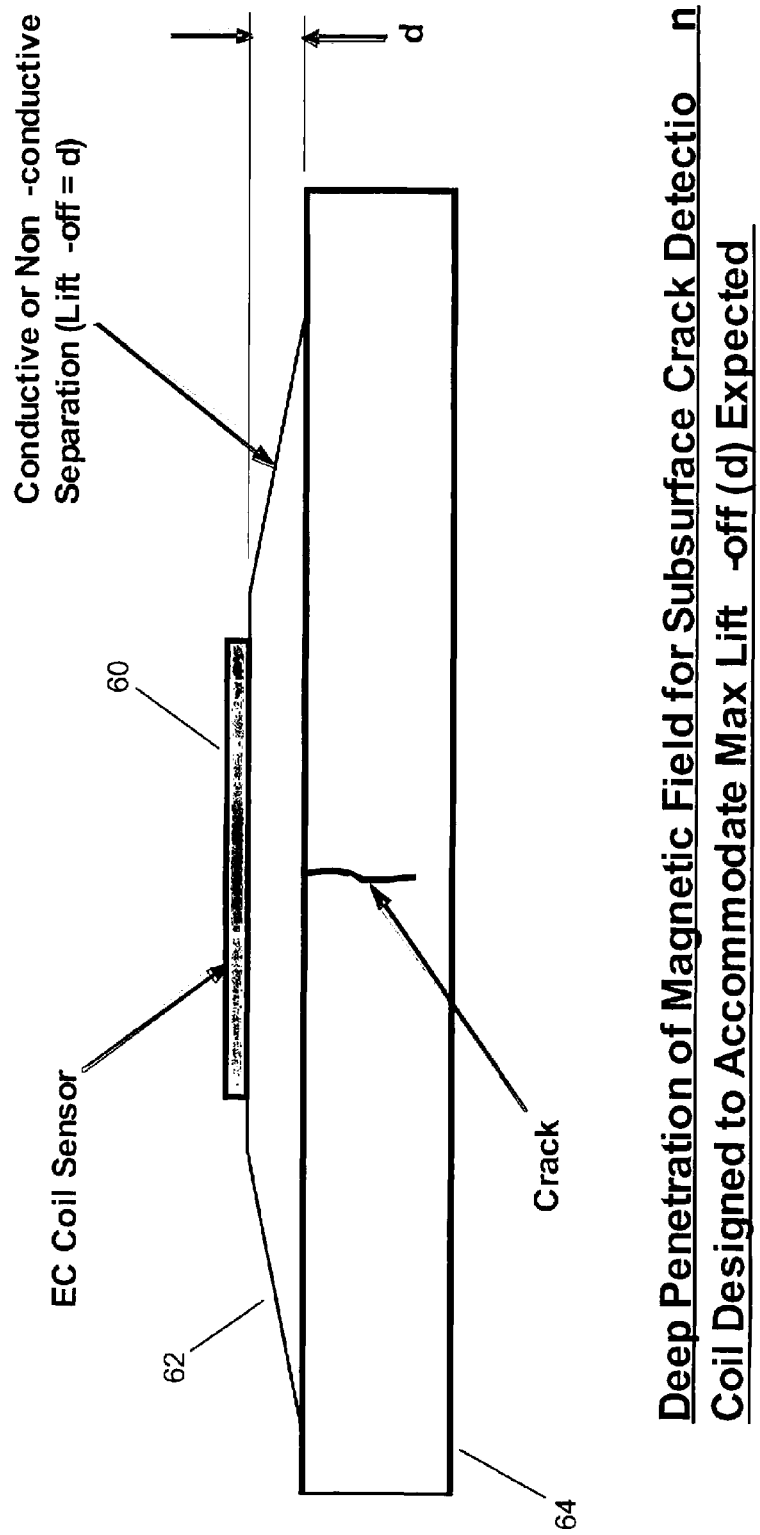
FIG. 24 shows an EC Coil Sensor mounted on an underlying cracked structure, with an intermediate layer with a lift-off separation distance=d.

Referring to the basic dimensions of a rectangular planar coil in FIG. 23, where the coils's outer length, B, is much grater than the coil's outer width, D, (i.e., B>>D for a rectangle), this de-coupling effect occurs when the half-width of the planar coil, R, is greater than or equal to the lift-off separation distance, "d" from the coil to the surface of the underlying structure being inspected (see FIG. 24 for the definition of lift-off distance, "d"). We define the coil's half-width, R, as equal to ¼ of the sum of the inner width, C, and the outer width, D. Hence, R≧d.

$$R \geq d \quad \text{(eq. 2a)}$$

In other words, this de-coupling effect occurs when:

$$\tfrac{1}{4}(C+D) \geq d \quad \text{(eq. 2b)}$$

Or, equivalently:

$$C+D \geq 4d \quad \text{(eq. 2c)}.$$

For a circular planar coil, having an inner and outer radius, $R_i$ and $R_o$, the equivant mean "width" $R=\tfrac{1}{2}(R_i+R_o)$. Hence, decoupling occurs when:

$$\tfrac{1}{2}(R_i+R_o) \geq d \quad \text{eq (3)}.$$

In the case of conductive structures, the coil of the invention is not lower-bounded in frequency and can operate in sufficiently low frequencies to penetrate through a structure of reasonable thickness and still produce eddy currents in the structure of interest. The depth of penetration is determined by the skin effect and is inversely proportional to the conductivity of the material and the frequency of the current flow. Also, the phase lag of the coil response can be measured to determine the depth of the signal and confirm that the defect is located in the structure.

$$\delta = \sqrt{\frac{2}{\omega\mu\sigma}} \quad \text{(eq. 4)}$$

Figure 8:
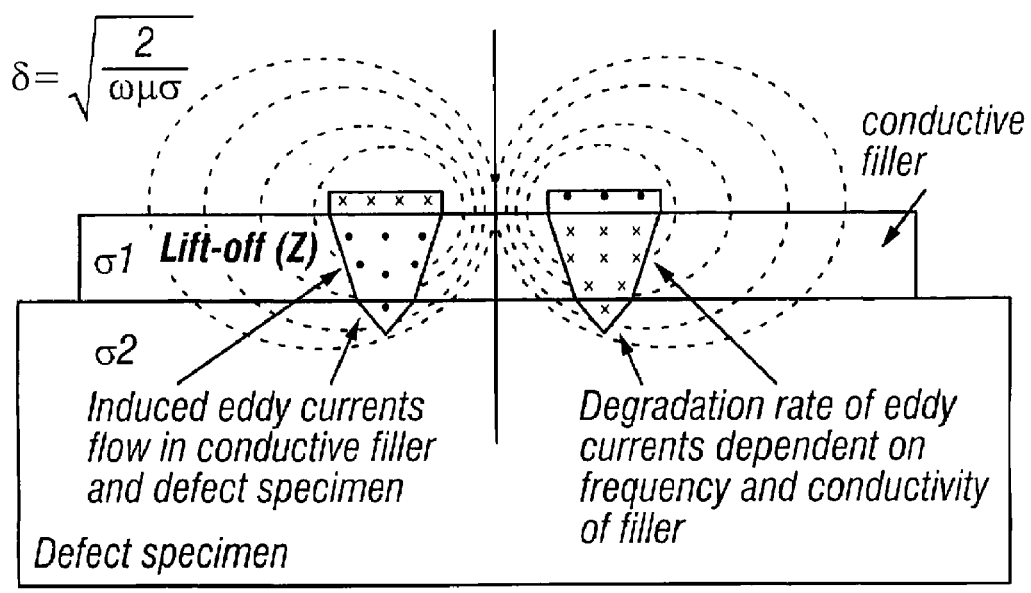
FIG. 8 illustrates impact of conductive filler on eddy currents in a structure.

Nevertheless, it is a common mistake to confuse the skin effect phenomenon with proximity. The skin effect only determines the penetration of the eddy current within the structure as function of frequency and the material's conductivity. As illustrated in FIG. 8, the drive electronics in the invention can lower the coil's operating frequency to "push" the eddy currents deeper into the structure to locate subsurface defects and whether a crack has gone completely through a structure. For a conductive filler, one should select an "omega" such that delta (omega, sigma 1) is greater than the thickness of the conductive filler. Access to the defect specimen can be confirmed by observing a change in phase in the received signal as the frequency is lowered (omega/2/pi); this indicates that the defect specimen begins to influence the coil response.

Manual inspection techniques used in time-based maintenance are user dependent; the measurements taken depend significantly on the device settings, the probes used, the scanning direction, the scan rate, and the ability to maintain a steady hand. As shown in FIG. 8, these factors introduce significant errors, raising the noise floor of time-based data sets sufficiently to hide incipient damage. A mountable, in-situ sensor, however, is able to cover a similar region of interest without the need for scanning, and thereby eliminates many of the noise factors described above. Furthermore, the data collected can be calibrated to reduce time-varying factors (e.g., temperature) with minimal effort. The result is greater sensitivity to detect small cracks and the ability to find damage much earlier; potentially at a point where repairs are less expensive and more reliable.

The coil is one aspect of the in-situ sensor of the invention. The system of the invention incorporates other needs that characterize a SHM system, namely being remotely addressable, self-operating, long lasting, and data recording. It is preferably completely self-contained and supports either wired or wireless interface for configuration, data-uploading, or real-time measurements. It can operate from batteries for at least a full year and alter its measurement rate to adjust to the bandwidth of the environment being sensed. It can perform period self-calibration and self-test to ensure valid data. It can also switch among measurement modes to provide event detection and detailed measurements.

Figure 9A:
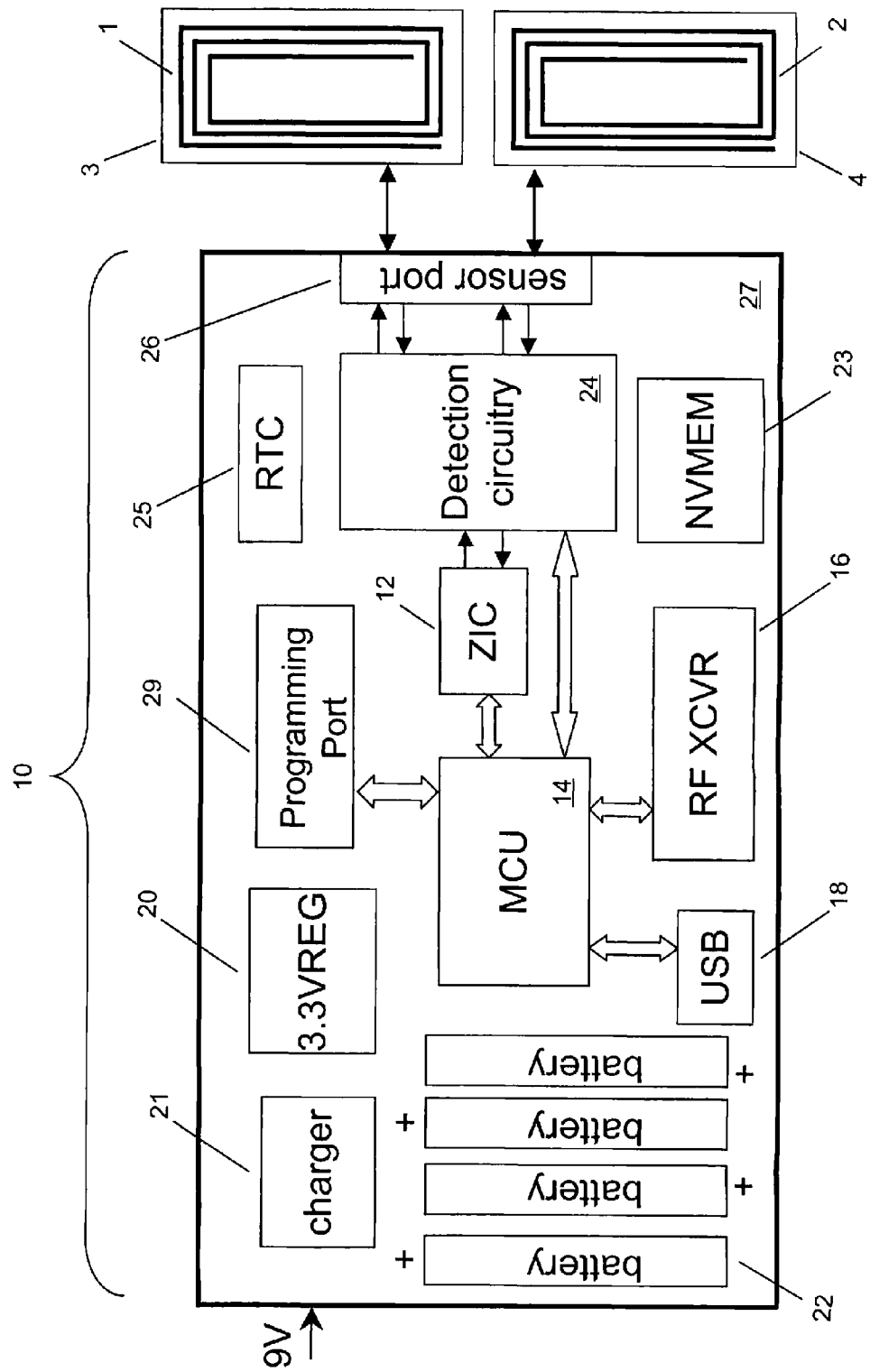
FIG. 9A is a schematic diagram of a preferred integrated sensor of the invention driving two coils.

One embodiment 10 of an eddy current sensor system of the invention is shown in FIG. 9A. The system 10 of the invention shown in FIG. 9A drives, for example, a pair of planar eddy current sensor coils 1, 2, mounted on supporting substrates 3 and 4, respectively. The number of driven eddy current coils can be one, two, or greater than two. System 10 can include: Impedance Integrated Circuit (IC) 12 to drive and measure the coils responses; micro-controller unit (MCU) 14 to control the Impedance IC, collect, and process the data, manage external communications, control the mixed signal circuitry, and provide power management; a wireless transceiver (RF XCVR) 16 to obtain configuration information and upload stored data, and provide real-time measurements; a USB/UART port 18 to manage wired communications (other possible direct input/output ports include standard serial or parallel ports); power management block 20 to regulate system power, determine remaining charge, and recharge batteries 22; charger 21, detection circuitry 24 for event detection and differential bridge measurements; a sensor port 26 to provide multiple sensor coil inputs from sensor coils 1 & 2; Non-Volatile Memory (NVMEM) 23 for storing data; a Real Time Clock (RTC) 25; and a Programming Port 29 for re-programming the MCU 14. Other options (no shown) can include a waterproof case and LED status indicator lights. All of the circuitry described above is mounted on a common insulating substrate 27, such as a printed circuit board (PCB) or printed wiring board (PWB). Substrate 27 can be rigid, semi-rigid, or flexible, depending on the material and/or thickness.

Figure 9B:
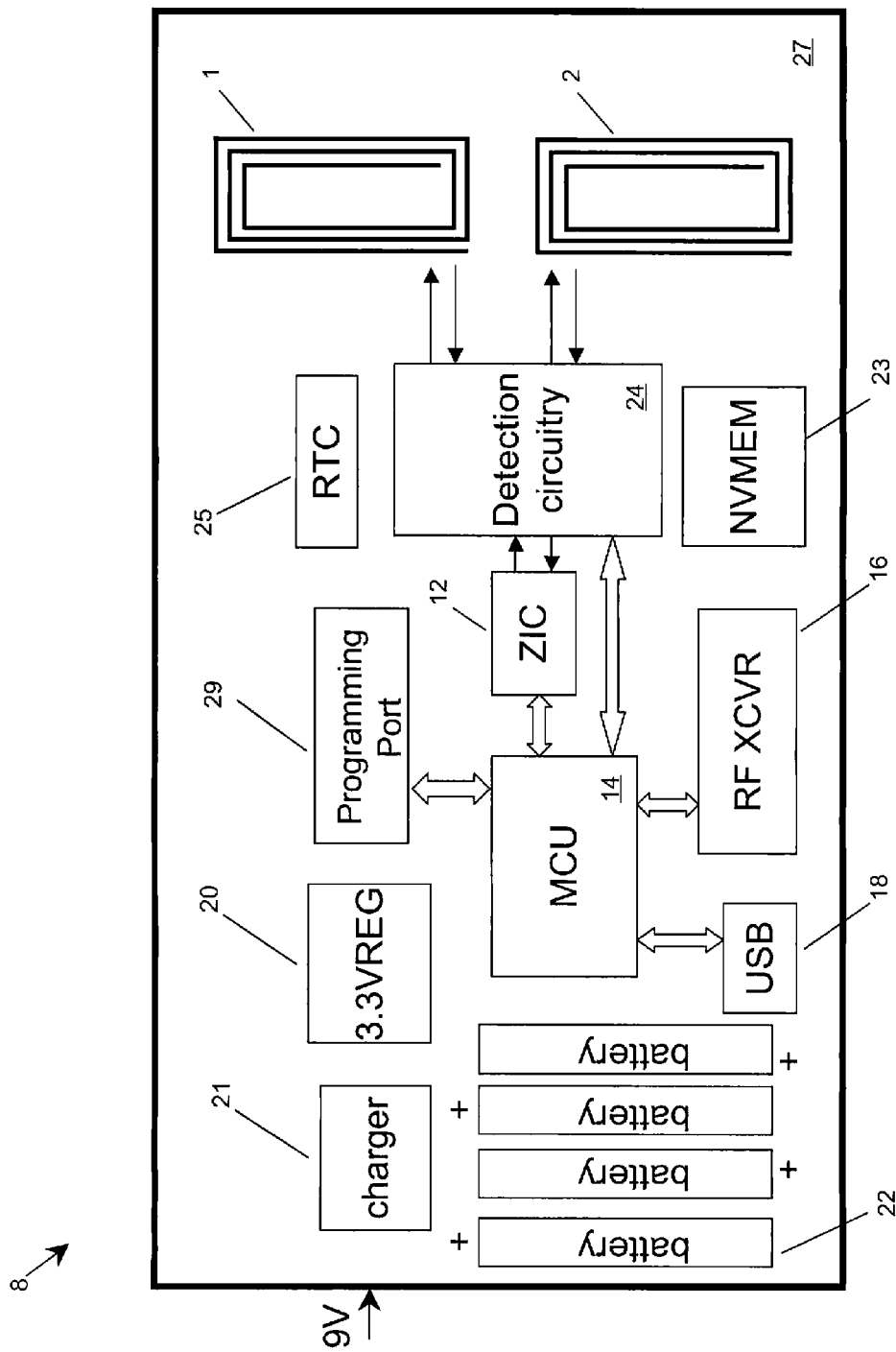
FIG. 9B is a schematic diagram of a preferred integrated sensor of the invention driving two coils.

A different embodiment, 8, is shown in FIG. 9B, which is the same as described above in FIG. 9A, except that the pair of planar EC coils 1 and 2 are mounted on the same insulating substrate 27 (e.g., PCB, PWB) as the rest of the electronic circuitry. In this sense, the sensor coils 1 and 2 are physically integrated along with the crack detection circuitry, disposed onto a common insulating substrate 27. Substrate 27 can be a thin, flexible insulating material such as Kapton, or other electrically insulating polymeric material. In one embodiment, the system 8 shown in FIG. 9B has a small form factor, on the order of 2 inches×2.5 inches×0.625 inches thick; and can operate for at least 3 months from 2 AA batteries, and has a minimum 60 kB flash memory, and is lightweight and inexpensive to manufacture, using printed circuit board fabrication techniques.

Figure 9C:
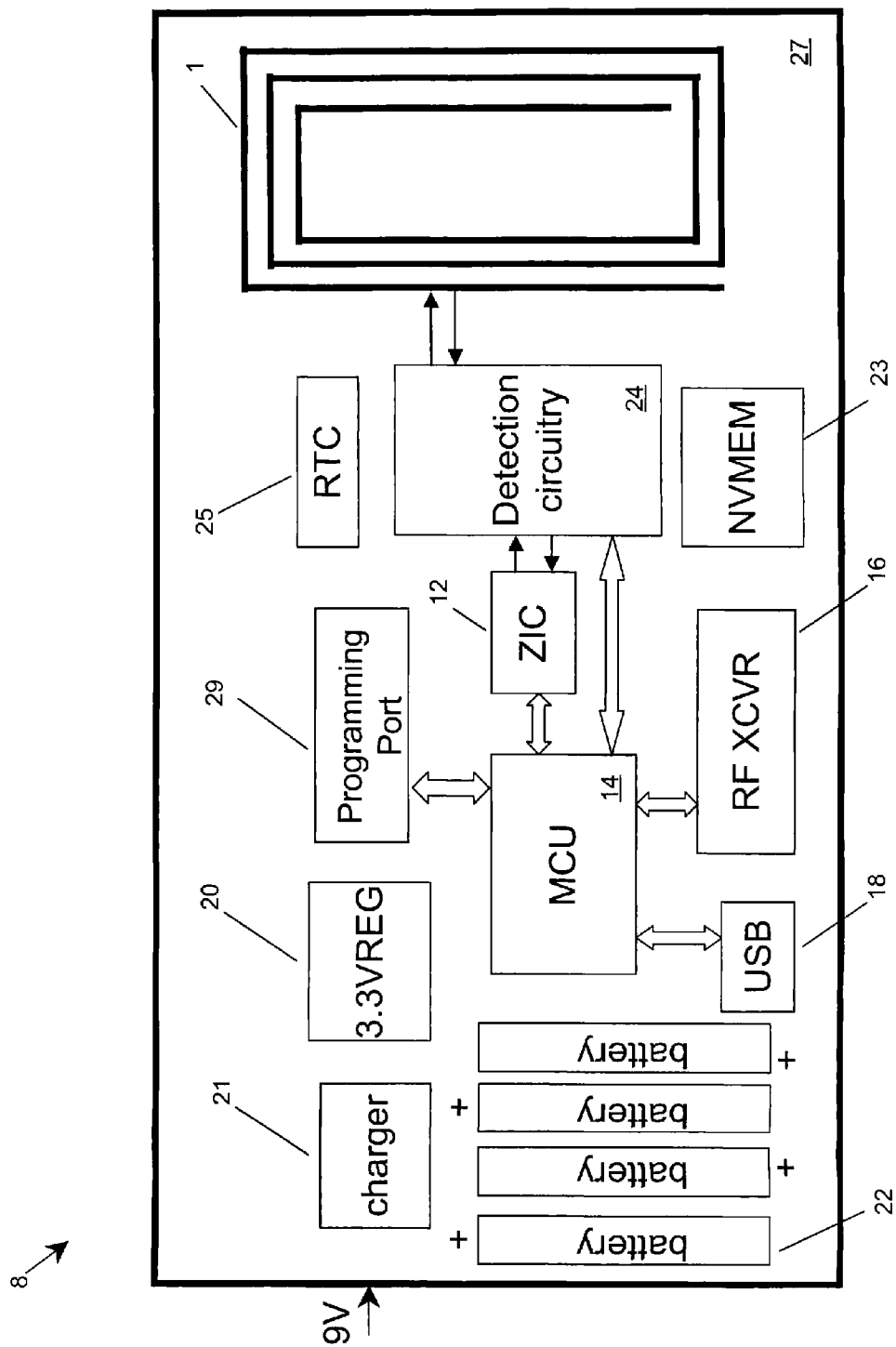
FIG. 9C is a schematic diagram of a preferred integrated sensor of the invention driving one large coil.

FIG. 9C shows another embodiment, the same as in FIG. 9B, except that there is only a single, large planar EC coil 1.

Figure 9D:
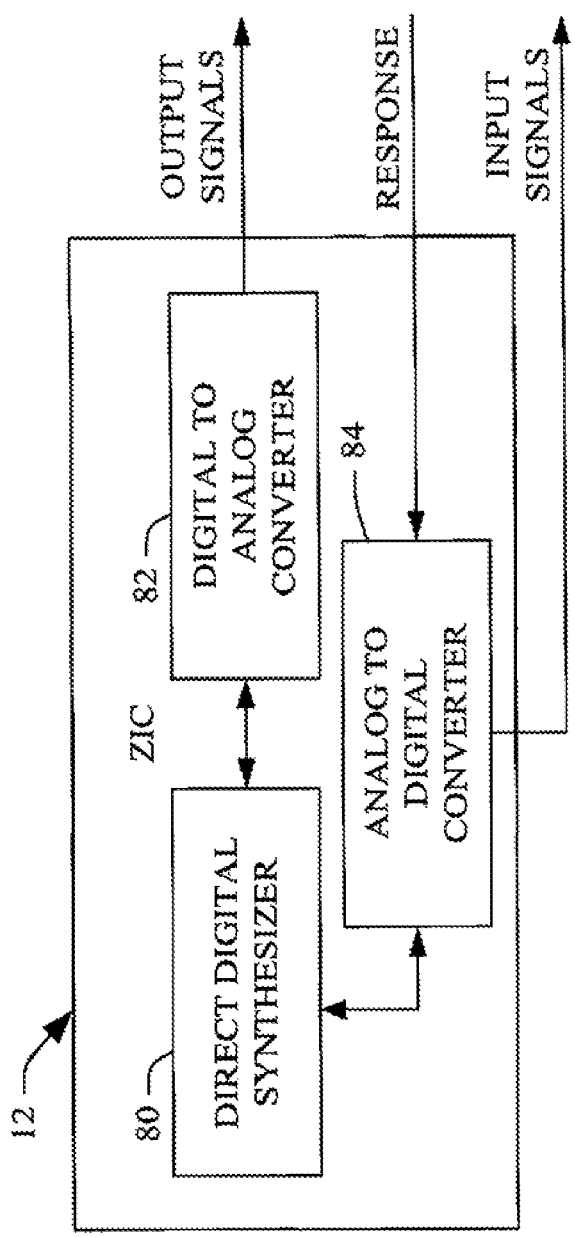
FIG. 9D is a functional block diagram of modules in an impedance integrated circuit that may be included in an integrated sensor.

Referring to FIG. 9D, exemplary circuitry in the Impedance Integrated Circuit 12 is illustrated. The Impedance Integrated Circuit 12 includes a direct digital synthesizer 80 and digital-to-analog converter 82 that generate output signals for provision to the planar eddy current coil. The Impedance Integrated Circuit 12 also includes an analog-to-digital converter 84 that receives response signals from the planar eddy current coil and digitizes the response signals to generate input signals, wherein said analog-to-digital converter 84, said digital-to-analog converter 82, and said direct digital synthesizer 80 are synchronized.

The planar coils can be made of copper, silver or gold, or other conductive material. A capacitor can be integrated directly into the coil to provide a resonant circuit. The coil traces can use a trace width that is much greater than its thickness to minimize the resistance of the traces. The coils can be arranged in a rectangular geometry where the length is at least twice as large then it width, and the coil can be oriented with its length orthogonal to the path of a future or anticipated crack growth. The dimensions of the planar coil can be selected to be proportional to the displacement (i.e., lift-off distance) between the coil and the structure under inspection. The width of the inner coil winding can be twice the distance between the coil and the material under inspection, when the medium between the sensor and the material under inspection is non-metallic and non-magnetic. The square-root of the desired number of turns in the coil determines the number of layers and turns per layer. This approach provides the optimal inductance versus resistance trade-off.

Functionally, the system generates an excitation waveform to drive the reference and test coils, uses detection circuitry to amplify the differential response, digitizes the analog waveform, and performs frequency-based transformations to generate a complex response that can be compared temporally and communicated to a remote device that can plot the response (see FIG. 10).

Impedance analysis is the process of determining the impedance characteristics of an unknown component. This process is performed by injecting current, at a particular frequency, into the unknown component and measuring the corresponding difference in magnitude and phase between the received signal voltage and the transmitted (or injected) current. The change in magnitude provides information on the amount of attenuation (or gain) introduced by the component. The change in phase indicates whether the component is inductive (lagging phase: current lags voltage) or capacitive (leading phase: current leads voltage) or resistive (no phase change). However, when performing defect detection in specimens, the goal is not to measure the absolute value of the component's impedance; it is desirable to measure changes in impedance that may be the result of damage. These changes are minute and require precision to capture tiny impedance variations.

One method to improve precision is to synchronize the components that are used to generate the injected current and measure the received voltage. Synchronization removes any timing differences or drift between the transmitted signal and the received signal. Timing differences correspond to phase jitter that makes the signal appear with phase distortion. This phase distortion, or phase noise, creates a floor that limits the phase resolution of the equipment. Drift can be caused by using different clocks (or oscillators) for the transmitter and receiver. A frequency offset will make the receive signal appear to drift at a rate corresponding to the offset. This drift is often reduced with the use of a phase-lock loop that synchronizes the receiver's clock with the received signal.

Fortunately, these problems are eliminated when the transmitter and receiver use the same clock to generate the transmitted signal and sample the received signal. The coherent or "synchronized" system therefore will exhibit much lower phase noise and doesn't require a phase-lock-loop to eliminate drift.

In one embodiment, the present invention comprises: An eddy current sensor system apparatus for inspecting surface and sub-surface faults of a structure, said apparatus comprising: a direct digital synthesizer and digital-to-analog converter to generate output signals; an analog-to-digital converter to digitize input signals, wherein said analog-to-digital converter, said digital-to-analog converter, and said direct digital synthesizer are synchronized to provide coherent detection; and circuitry for calculating the voltage ratio and phase shift between the input and output signals.

Figure 22:
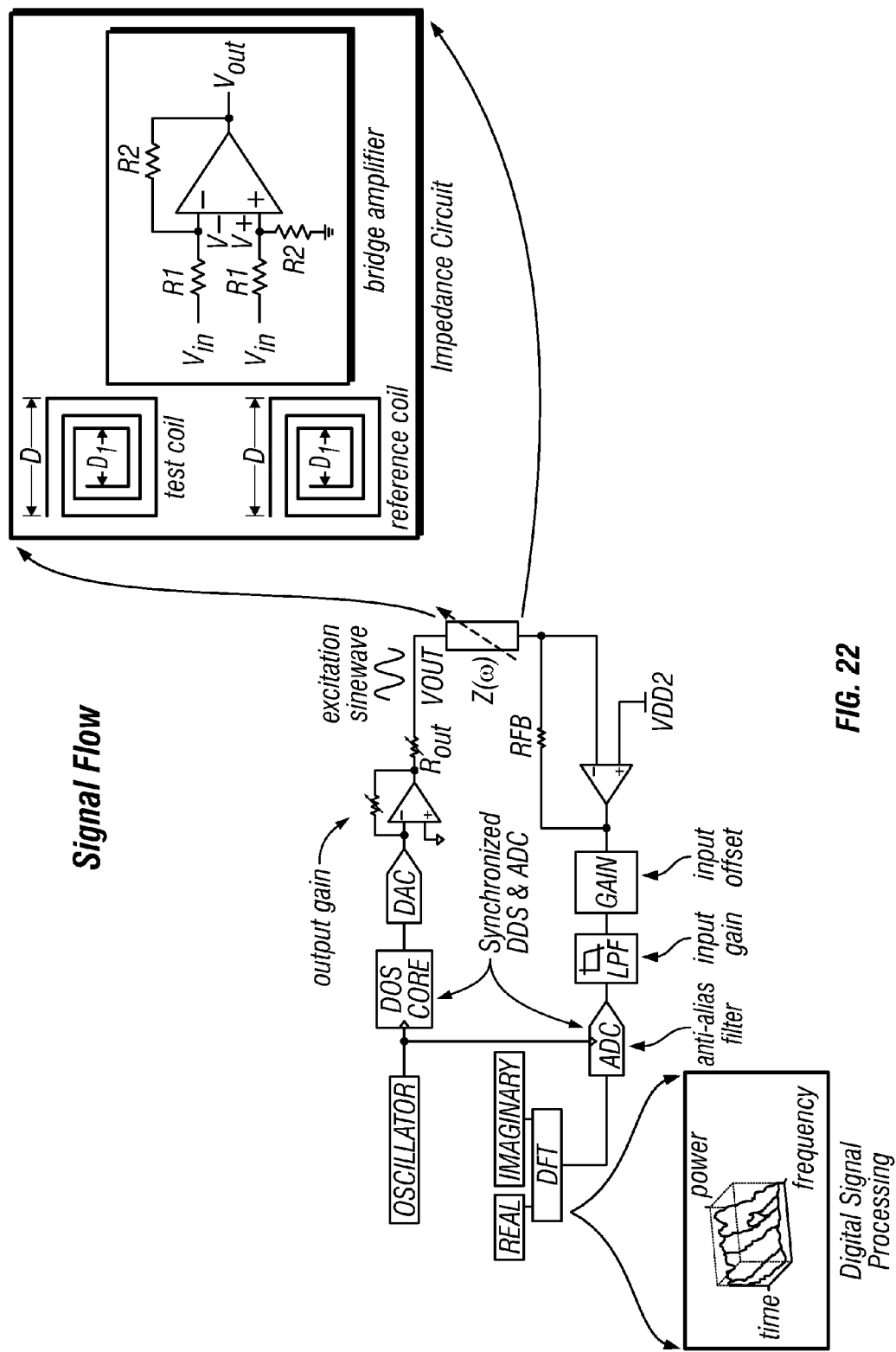
FIG. 22 shows a signal flow path for the invention.

FIG. 22 shows an example of a signal flow path for the invention.

An impedance plane display showing phase and amplitudes of EC signals generated by cracks of varying depths illustrates a rotated response so that the lift-off axis is oriented horizontally rather than vertically. Also the inspector will preferably amplify the response and place the apex of the operating region in the lower right-hand corner. This operating region represents a point along the curve in FIG. 3. Magnitude and phase response of the coil behave in an understood manner with increasing depth. The device can also adjust the voltage of the signal to mimic the lift-off effect. This can be used to determine the detection area of the device and amplify movements that are not related to lift-off effects.

Figure 11:
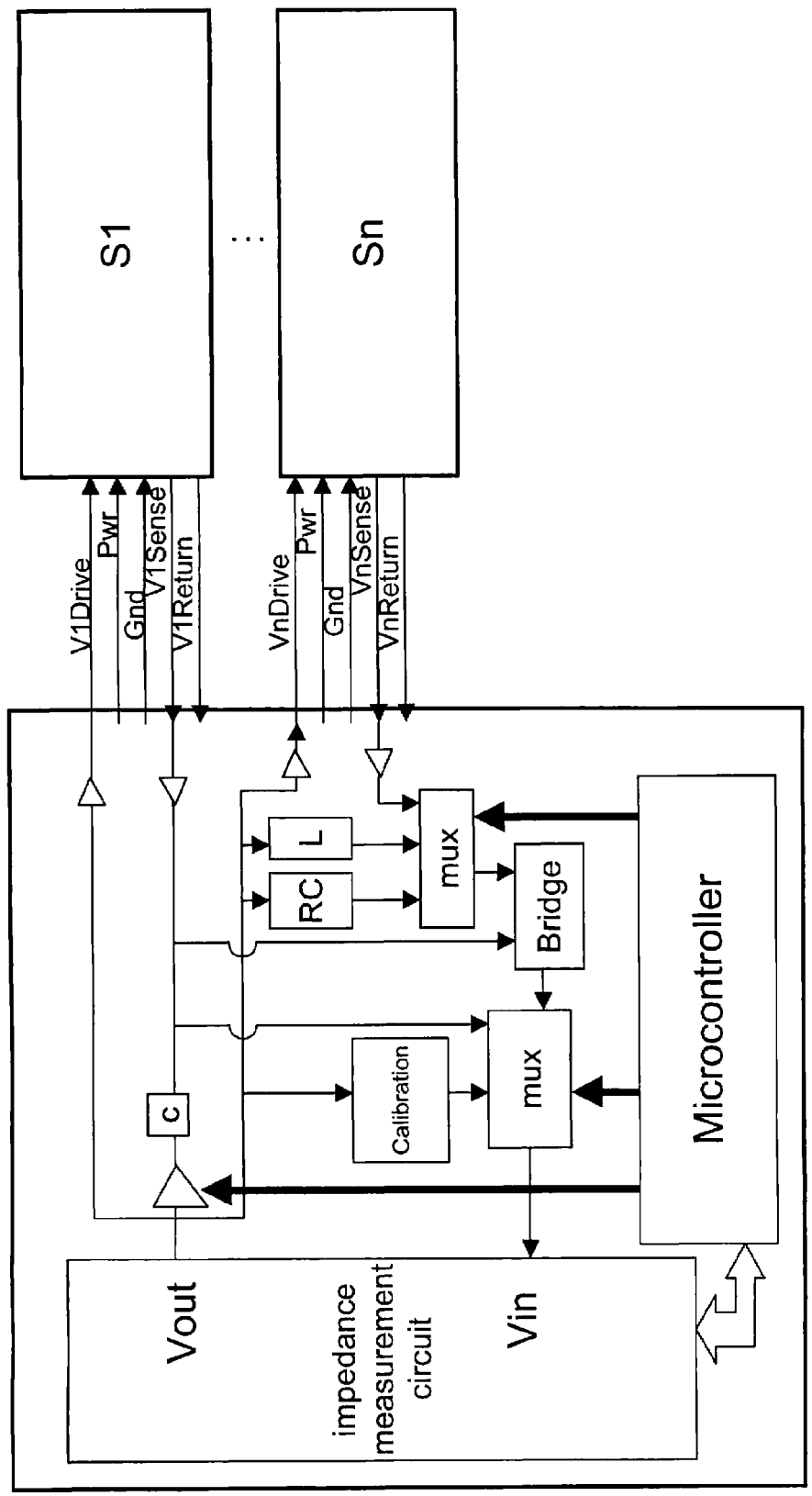
FIG. 11 is a schematic diagram of signal mixing circuitry according to the invention.

Taken as a whole, the system provides a powerful tool that can grow to accommodate new processing algorithms, provide real-time assessment without human intervention, and select from a variety of measurement configurations to "zoom" in or out when inspecting a structure. FIG. 11 illustrates the mixed signal blocks 28 that permit multiple operation modes for either event detection or differential measurements to provide dynamic resolution.

When mountable sensors, according to the invention, are placed in position, they can be used to collect data more frequently than permissible by manual inspection techniques. As a result, the fixed sensor is more likely to see fewer fluctuations in the acquired data and any fluctuations can be filtered away. Additionally, the measurement frequency (i.e., sampling rate) can be increased to correspond with the growth in the fatigue crack. This approach can extend battery life by a significant factor over designs with a fixed measurement interval, without losing any detail.

To make any remote measurement device reliable, it must be able to compensate for temperature drift. The AD5933 impedance IC also contains a thermistor that can be used to provide temperature compensation for the measurements. During the initial days of operation and at pre-defined intervals, the eddy current sensor performs more frequent impedance and temperature measurements. A regression analysis of the data is then used to determine a reliable temperature coefficient to offset the temperature deviation for subsequent measurements. Furthermore, responses to crack growth are not to expected to oscillate and will represent a shift in the operating point, rather than a oscillatory event like temperature and other diurnal variations.

The device can be re-configured and calibrated to accommodate a number of different modes of operation. Note that these modes can be operated either in manual or automatic mode.

Event Detection Mode. In its simple form, the system can configure the sensor in a tank circuit that can detect changes in the Q or resonant frequency of the sensor. This approach is used in many detection systems because it requires minimal complexity.

Direct Impedance Mode. Most commonly, the device can be used like the Nortec 1000's eddy current sensor to monitor impedance plane curves in real-time. This configuration allows the user to verify the operation of the coil and system by observing the changes in the impedance plot when the coil is moved around the structure in both the horizontal and vertical axis. Upon event detection, the system can reconfigure the sensor to perform direct measurements using a differential bridge circuit to maximize dynamic range.

Calibration Mode. In calibration mode, the user can make in-situ measurements to calibrate the system directly by determining the adjustment factors to compensate for offsets in component values. The calibrations can be made with the aid of sealed inductors that should not be affected by the structure, nor should drift excessively over time.

Data Storage and High Pass Filtering. For in-situ structural health monitoring, the embedded eddy current sensor can be programmed to make periodic measurements. In this case, the user defines the frequency of operation and the measurement interval. Running a high pass filter of the collected data reveals significant events that require further attention. Additionally, low pass filtering of the data indicates any insignificant deviations that can be removed from the measurements.

Remote, Real-Time Monitoring and Event Alarms. Finally, in many circumstances, the structure under inspection is located in a remote area and it is desirable to limit the number of visits to inspect the structure and retrieve data from the device.

The device preferably operates on battery power, stores several weeks of measurements, and provides a wireless communication link for remote access. The invention preferably utilizes the Zigbee wireless protocol reference standard to transfer data when it is not connected to a PC, and has been configured for remote operation. A range extender can be used to extend the range of the system to a radius of 5 miles. In cases of where cellular coverage is present, it may be desirable to use a cellular OEM module to communicate via the cellular network.

To maximize battery life, the system preferably employs a limited wireless connectivity scheme. After executing a predefined number of measurements, the device will invoke the transceiver and search for its host device. If not found, the transceiver will shut-down until the next cycle of measurements is complete.

When a host device is identified and validated, the host device will inquire about the status of the embedded eddy current device. Depending on the mode of operation, the host device can either upload and post-process the information, or plot the information in real-time to permit the user to directly evaluate the state-of-health of the structure. Subsequently, the host device can begin to interact with the remote device to retrieve data, reconfigure, recalibrate, or perform other functions.

The tabulated information in Table 1 compares the major impedance measurement approaches, advantages, disadvantages, frequency ranges, and applications. Given an operating frequency of 50 to 100 kHz, the auto-balance bridge method provides the best measurement accuracy.

TABLE 1

Comparison of previous impedance measurement techniques

| Technology Application | Advantage | Disadvantage | | Frequency range |
|---|---|---|---|---|
| Auto-Balancing-Bridge | Most accurate Wide impedance measurement range Wide frequency coverage measurement Probing Measurement | Limited frequency coverage and impedance measurement range | 5 HZ-40 MHz 100 MHz | All impedance measurement applications in LF (4194A, etc.) measurement 4194A + 41941A, etc.) |
| RF I-V | Accurate impedance measurement through the GHz range Grounded device measurement | Limited frequency coverage | 1 MHz-1.8 GHz | Components and materials measurement in RF (4291B, etc.) |
| Network analysis | Very broad frequency coverage (LF through microwave) | Impedance measurement range is limited to values close to the characteristic impedance of the analyzer. | ≧10 kHz | Components and materials measurement (8753E, E5100, etc.) |

Figure 12:
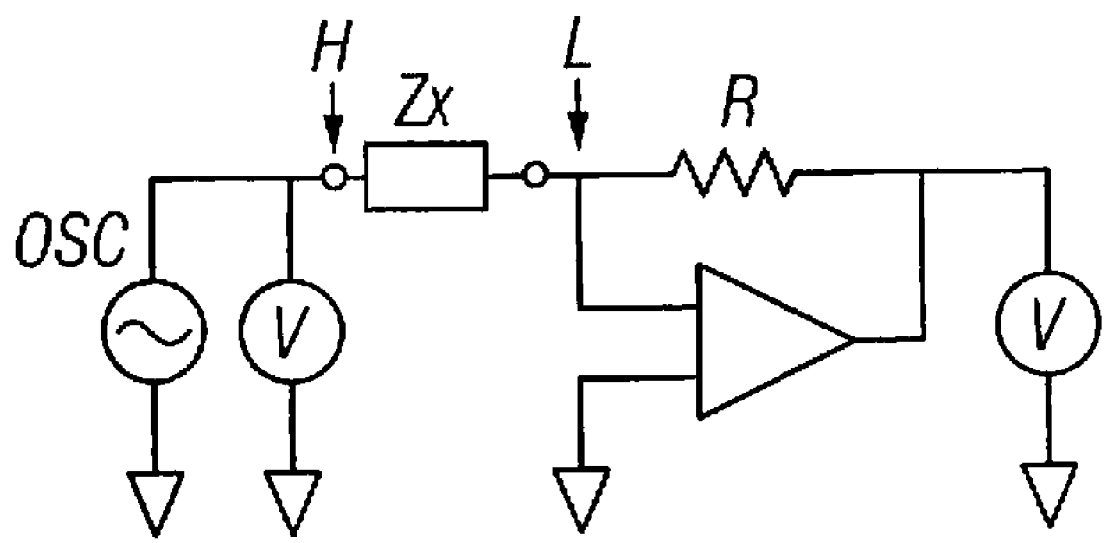
FIG. 12 is a schematic diagram of a preferred auto-balance bridge useful with the invention.

A simple, single-element bridge, as depicted in FIG. 12, consists of an oscillator, the unknown impedance, an operational amplifier, and a feedback resistor. The input and output of the bridge circuit are fed into analog-to-digital converters (ADC) where measurements can be made. The circuit seeks to measure the voltage ratio required to balance the current flowing through the unknown impedance with current flowing through the feedback resistor. The circuit also measures the phase shift between the measured voltage and the source voltage. Given the magnitude and phase, the real (resistive) and imaginary (reactive) component of the unknown impedance can be determined. Although simple, this design has poor gain accuracy and also unbalances the bridge due to loading from the feedback resistor and op-amp bias current. Additionally, the output is non-linear.

Figure 13:
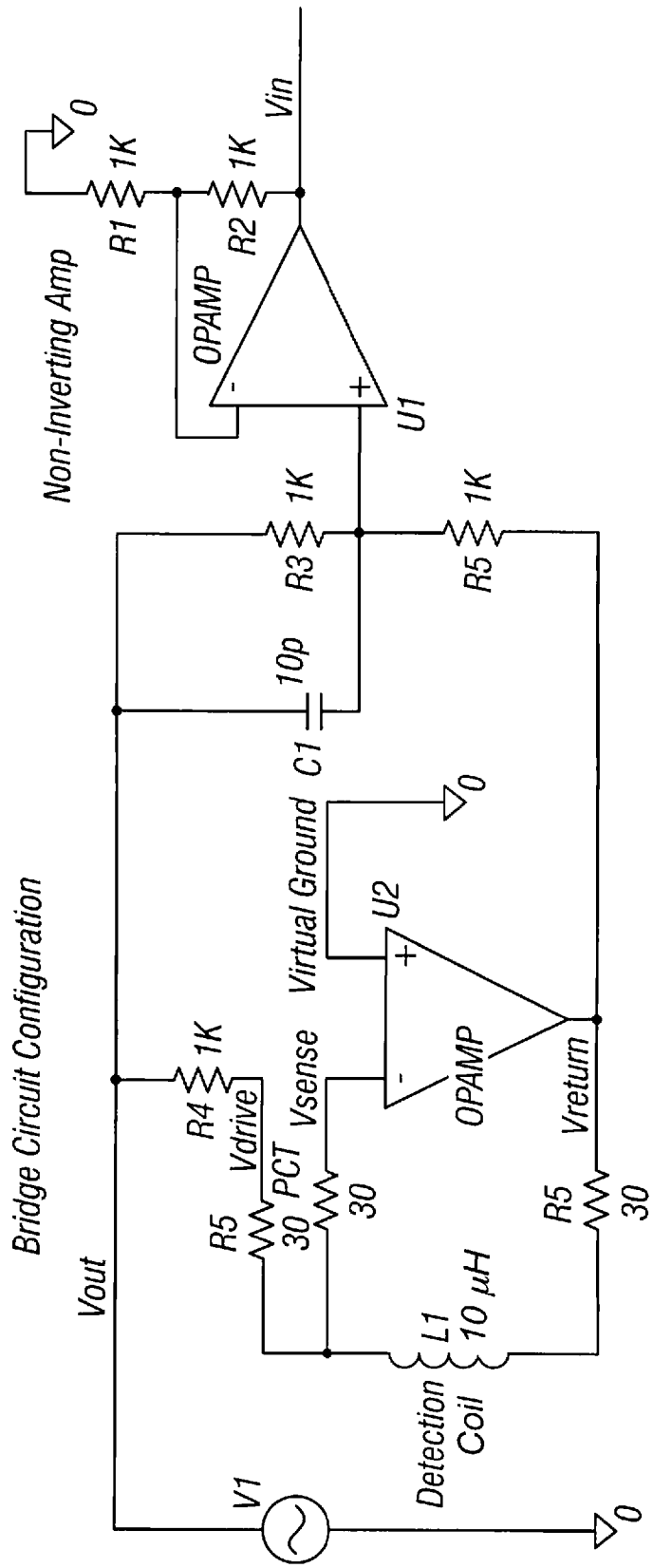
FIG. 13 is a schematic diagram of a preferred linear response bridge amplifier circuit of the invention.

However, in the case of crack-detection, it is necessary to measure small changes in the coil's impedance that are a result of crack growth directly underneath the coil. As a result, a bridge amplifier circuit is required. The design shown in FIG. 13 uses an op-amp to generate a virtual ground between the impedance elements in the primary branch and a second non-inverting op-amp that measures the voltage at the node of the impedance elements of the secondary branch. The RC impedance in the secondary branch offsets the LR impedance of the coil in the primary branch. The output of the bridge is digitized and stored as reference to compare against subsequent measurements. Additionally, three wires are used to connect to the coil to minimize the impact of the wire resistance for the remote coil.

The electronics for data logging, data analysis and data transmission preferably allow for autonomous flaw detection and the ability to automate the entire process such that a web site or person could be notified if and when human intervention is necessary.

Figure 25:
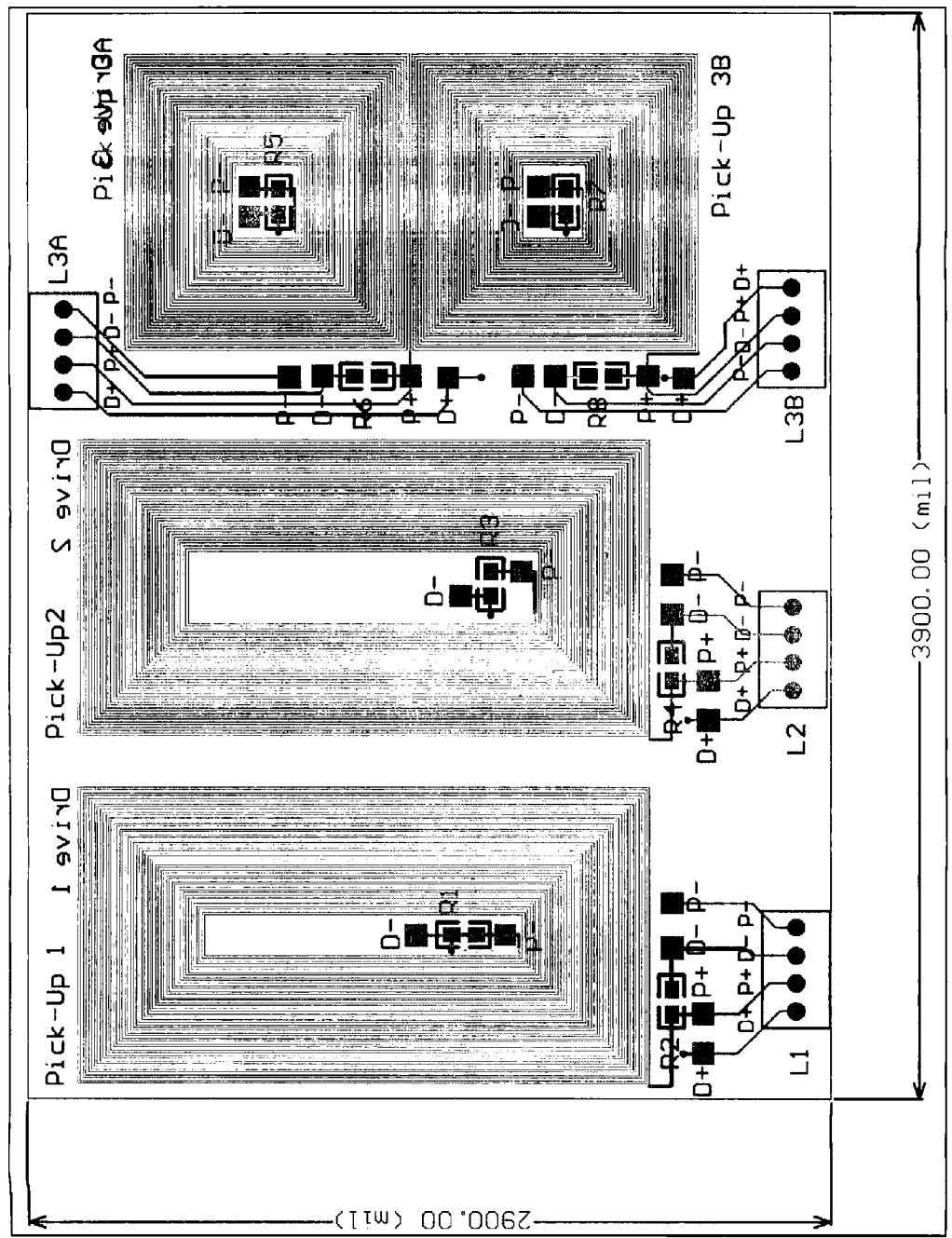
FIG. 25 shows printed circuit board layouts of prototype planar EC coils.

Prototype Planar Coil Design. FIG. 23 shows the basic layout and dimensions of a rectangular planar EC coil design. Combining the above insights, prototype planar coil parameters were derived numerically to optimize the Q of the coil. The actual CAD layout for the prototype coils that were fabricated and tested is shown in FIG. 25. Additionally, estimates of the capacitance were used to determine the self-resonant frequency of the coil. This measurement is important because it determines the valid range of operation. The model was used to generate a prototype planar coil with 41 turns, and the following dimensions:

B=1068 mils (27.12 mm), D=2073 mils (52.65 mm)
C=198 mils (5.029 mm), A=1782 mils (4.526 mm)
Trace width (E)=8 mils
Trace spacing (F)=8 mils
Layers=2
SRF=1.9 MHz
C=26.4 pF
L=261.6 µH
R=20.4 ohm Measurements taken with the HP4194A impedance analyzer provided the following results:

SRF=533 kHz
C=339 pF
L=263 uH
R=34.8 ohm
Q (100 kHz=4.72)

The detection capabilities of the $1^{st}$ prototype planar coil were verified with the use of a function generator to drive the coil and oscilloscope to monitor changes in amplitude and phase while moving the coil a fixed displacement over a test specimen containing a crack. This first prototype coil was designed to span lift-off gaps of 0.5 inches, and the mean width of the coil is about 1 inch.

Subsequent modifications to the $1^{st}$ prototype model indicated that higher Qs can be achieved by reducing the number of turns, increasing the number of layers. The fewer turns reduces the length, and corresponding resistance of the coil, while the additional layers increase the self resonant frequency of the circuit. Hence, the inductance of a multi-turn, single layer coil can be maintained with fewer turns and multiple layers.

Results for a $2^{nd}$ prototype coil were obtained by a coil design with a radius (mean width) greater than the lift-off displacement from the structure. The sensor can provide significant response at extensive lift-off, while a pencil probe and spot probe falter because they cannot maintain their sensitivity while trying to interrogate a structure beneath thick lift-off layers.

Inspection performance results for the prototype sensor design are shown in FIGS. 14 and 15. These impedance plots show the overall sensitivity of the mountable sensor as it detects cracks located through increasingly thick lift-off layers up to 0.98" thick. Note that these plots also include the signals produced by the sensor when placed in an unflawed region. Such signals from unflawed regions correspond to the noise in the sensor; so it is desirable for the sensor to produce extremely small signals in unflawed regions. By comparing the signal levels at cracked and uncracked regions, it is possible to assess the sensitivity of the EC sensor using signal-to-noise (S-N) levels. Normally, flaw calls (i.e., detected cracks) can be made if S-N values exceed 3 (S-N ratio of 3:1). The results in FIGS. 14 and 15 show that even through extreme lift-off conditions (inspection impediment), the sensor produced a S-N level of 25:1 for the 0.98" lift-off distance. In fact, none of the S-N levels dropped below 10, indicating that the sensor is able to clearly detect all cracks.

Figure 19:
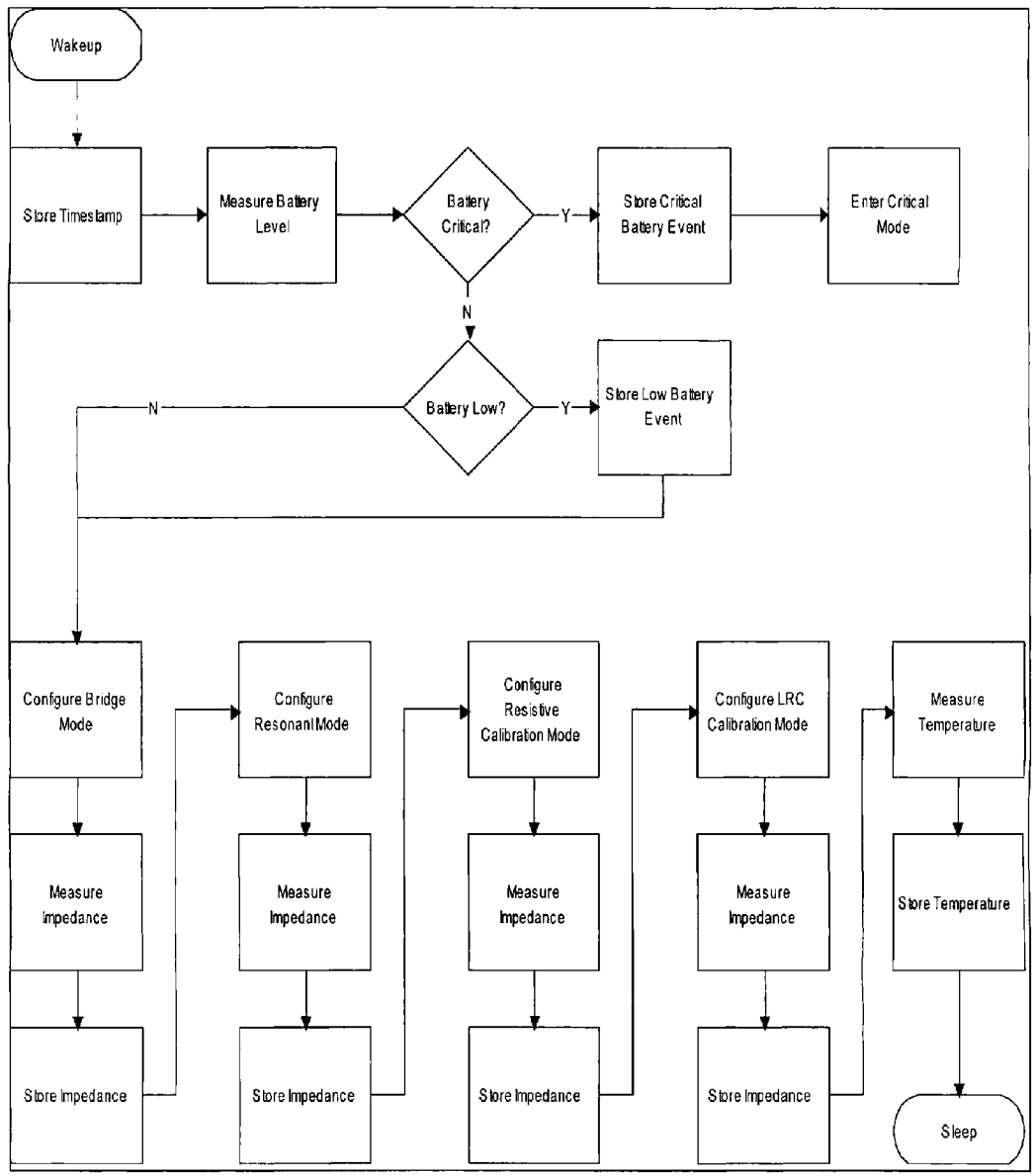
FIG. 19 shows a software flowchart describing sensor system function.

A flowchart of activities and features programmed into the operation of the sensor monitoring hardware is shown in FIG. 19. An external real-time-clock (RTC) is used to wakeup the system at pre-selected interrogation intervals to make measurements. Upon wakeup, the microcontroller unit (MCU) stores the timestamp and measures the battery level to determine if it is critical. If the battery has been depleted, the system enters a critical state where it minimizes activities and stops taking additional measurements. If the battery is not critical, but low, the system will record the event, and proceed with data acquisition. The system rotates between the two measurement and two calibration modes, each time configuring the impedance integrated circuit and storing the result in the external memory. After completing the impedance measurements, the MCU requests a temperature measurement from the impedance integrated circuit and stores it in the external memory, before reconfiguring the RTC and going back to sleep.

Figure 20:
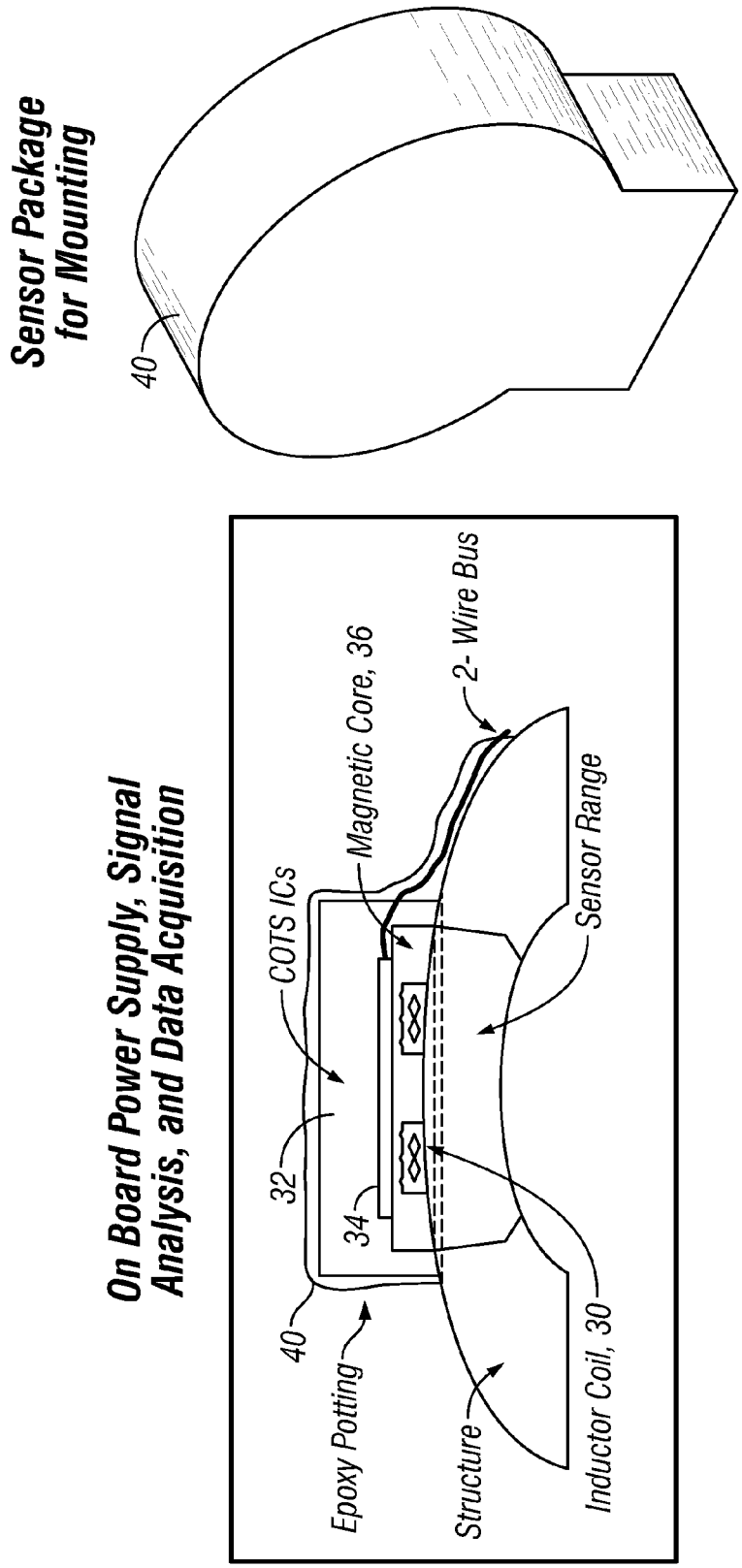
FIG. 20 shows a sample packaging approach for EC sensor with electronics.

In one embodiment, assembled system 40 as shown in FIG. 20 comprises sensor coil 30, and miniaturized electronics 32, disposed on a common substrate board 34. FIG. 20 illustrates an example package where sensor 30, placed on the bottom of board 34, would co-exist with electronics 32 on the top. Sensor coil 30 can be embedded or placed with a magnetic core, 36, for focusing the magnetic field. The entire sensor 40 can be potted in epoxy for protection from the environment. Sensors 40 would work independently and communicate with a hub to provide inspection results. To provide coverage for any large application, an array of sensors 40 can be distributed in critical regions.

Figure 21:
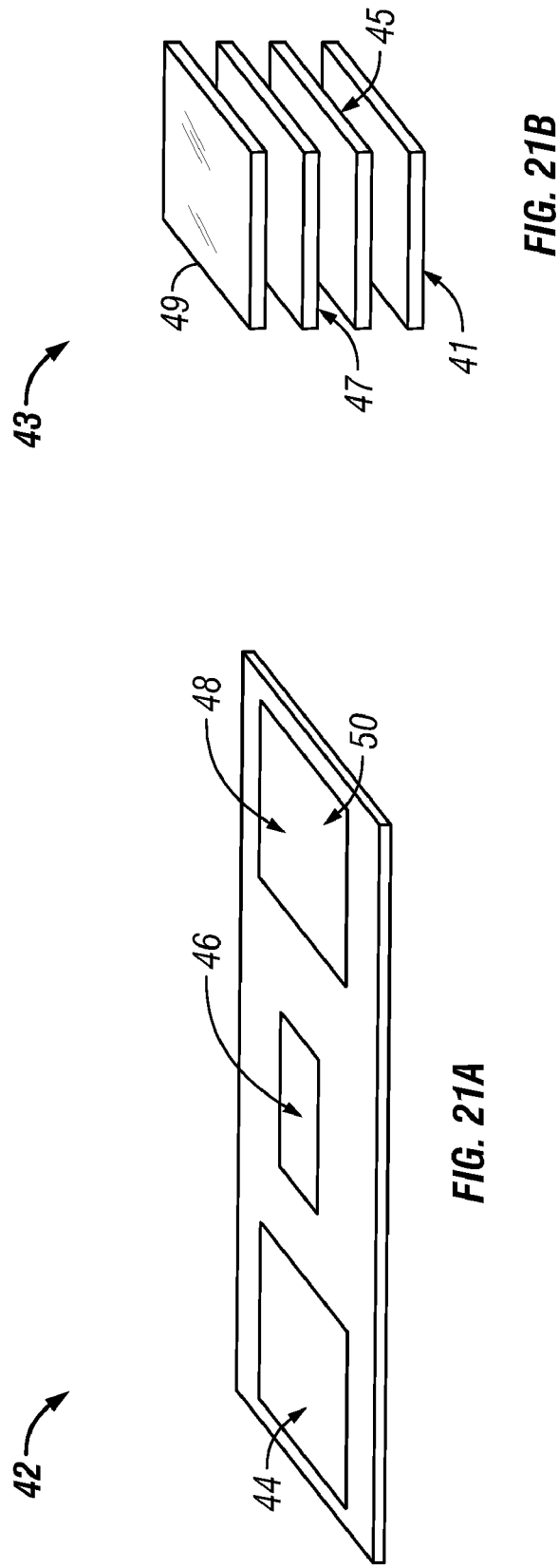
FIG. 21 shows an alternative EC sensor and control electronics package.

In another embodiment, assembled systems 42 and 43 as shown in FIG. 21A and FIG. 21B comprise sensors 44 and 45 electronics 46 and 47 and transceiver development path 48 and 49 respectively. FIG. 21A illustrates sensor 44, electronics 46, antenna 50 and transceiver development path 48 packaged on a common substrate, called a microsystem package.

If a reduction in overall footprint is necessary then a stacked package configuration, as shown in FIG. 21B, is preferably used. FIG. 21B preferably stacks a polyimide encapsulation as the bottom layer 41, then sensor 45 is stacked on top of bottom layer 41, then electronics 47 and finally transceiver development path 49 is the top layer of assembled system 43. The advantage of having the coil directly integrated with the printed circuit board (PCB) is that simplified manufacturing can reduce assembly costs and part count.

FIG. 23 shows a rectangular planar EC coil design.

FIG. 24 shows an EC Coil Sensor mounted on an underlying cracked structure, with an intermediate layer with a lift-off separation distance=d. Structure 64 has a crack in it. Covering the structure 64 is a layer 62 of a conductive or non-conduction material, such as a thick protective coating of epoxy paint, or a composite doubler plate (e.g., a boron epoxy composite repair plate), having a thickness=d. The EC coil sensor 60 is attached to this layer with, for example, glue of double-sided adhesive tape (not shown). The width of the ED Coil is sufficiently wide so as to effectively penetrate through the relatively-thick intermediate stand-off layer 62.

FIG. 25 shows printed circuit board layouts of prototype planar EC coils that were fabricated and tested.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A battery-powered eddy current sensor for inspecting surface and sub-surface faults of a structure, said apparatus comprising:
    a primary planar eddy current coil;
    a secondary planar eddy current coil;
    a direct digital synthesizer and digital-to-analog converter that generate output signals for provision to the primary planar eddy current coil;
    an analog-to-digital converter that receives response signals from the secondary planar eddy current coil and digitizes the response signals to generate input signals, wherein said analog-to-digital converter, said digital-to-analog converter, and said direct digital synthesizer are synchronized;
    circuitry for calculating a voltage ratio and phase shift between the input and output signals;
    wherein said circuitry comprises the primary planar eddy current coil, the secondary planar eddy current coil, and a bridge circuit that is configured to measure a differential impedance change between the primary and secondary planar eddy current coils; and
    a battery that provides electrical power to the direct digital synthesizer, the digital-to-analog converter, the analog-to-digital converter, and the circuitry for calculating the voltage ratio and phase shift between the input and output signals.

2. The sensor of claim 1, wherein said circuitry comprises a microcontroller.

3. The sensor of claim 1, wherein said circuitry is configured to uses a discrete Fourier transform to determine magnitude and phase of voltage of the input signal, and is further configured to compute a complex impedance based at least in part upon the magnitude and phase of the voltage of the input signal.

4. The sensor of claim 1, wherein said sensor operates over a range of frequencies from approximately 100 Hz to approximately 100 kHz.

5. The sensor of claim 1, wherein said bridge circuit as configured to cancel impedance changes common to both eddy current coils, and amplifies signals when mismatches in differential impedance between the primary planar eddy current coil and the secondary planar eddy current coil are detected.

6. The sensor of claim 1, additionally comprising a resonant circuit configuration comprising a capacitor in parallel with at least one of the primary eddy current coil or the secondary planar eddy current coil.

7. The sensor of claim 1, further comprising an LCR circuit that is employed to calibrate the response signals.

8. The sensor of claim 7, wherein the resistor in the LCR circuit is connected directly between the primary planar eddy current coil and the secondary planar eddy current coil.

9. The sensor of claim 1, wherein the circuitry comprises a high-pass filter that is configured remove diurnal measurement changes from measurement data.

10. The sensor of claim 1, wherein the circuitry additionally comprises low-pass filter that is configured to remove high frequency vibrations from the voltage ratio phase shift.

11. The sensor of claim 1, wherein said circuitry is further configured to determines battery discharge rate during operation of the sensor and is further configured to adjusts measurement intervals to maintain a desired period of performance between battery recharges.

12. The sensor of claim 1, wherein said sensor comprises at least one additional planar eddy current coil.

13. The sensor of claim 12, wherein said circuitry is configured to compare measured impedance of each eddy current coil to itself over time, and is further configured to compares measured impedance of the secondary planar eddy current coil against the other eddy current sensor coils.

14. The sensor of claim 1, wherein the primary planar eddy current coil, the secondary planar eddy current coil, the direct digital synthesizer, the digital-to-analog converter, the analog-to-digital converter, and the circuitry are integrated on a common substrate.

15. The sensor of claim 1, further comprising an antenna that is configured to exchange wireless communications with an external computer.

16. The sensor of claim 1, wherein a self-configurable sensor network comprises the sensor.

17. The sensor of claim 1, wherein the primary planar eddy current coil has a rectangular geometry.

18. The sensor of claim 1, further comprising double-sided adhesive tape that is configured to couple the sensor to the structure.

19. The sensor of claim 1, wherein said primary planar eddy current coil and secondary planar eddy current coil each have a geometrical shape of one of U-shaped, V-shaped, or C-shaped.

20. The sensor of claim 1, further comprising a real-time clock, wherein the direct digital synthesizer, the digital-to-analog converter, the analog to digital converter, and the circuitry are periodically activated based at least in part upon output from the real-time clock.

21. The sensor of claim 1, wherein the direct digital synthesizer is configured to generate the output signal such that the output signal has a range of frequencies, and wherein the response signals are indicative of severity and depth of a flaw in the structure.

22. A battery-powered eddy current sensor apparatus for inspecting surface and sub-surface faults of a structure, said apparatus comprising:
    a primary planar eddy current coil;
    a secondary planar eddy current coil;
    a direct digital synthesizer and digital-to-analog converter that generate output signals for provision to the primary planar eddy current coil;
    an analog-to-digital converter that receives response signals from the secondary planar eddy current coil and digitizes the response signals to generate input signals, wherein said analog-to-digital converter, said digital-to-analog converter, and said direct digital synthesizer are synchronized;
    circuitry for calculating a voltage ratio and phase shift between the input and output signals,
    wherein said circuitry comprises the primary planar eddy current coil and the secondary planar eddy current coil; and a battery that provides electrical power to the direct digital synthesizer, the digital-to-analog converter, the analog-to-digital converter, and the circuitry for calculating the voltage ratio and phase shift between the input and output signals, wherein the primary planar eddy current coil, the secondary planar eddy current coil, the direct digital synthesizer, the digital-to-analog converter, the analog-to-digital converter, and the circuitry are integrated on a common substrate.

23. The apparatus of claim 22, wherein said primary planar eddy current coil and secondary planar eddy current coil each have a geometrical shape of one of U-shaped, V-shaped, or C-shaped.

24. The apparatus of claim 22, wherein the substrate comprises a non-conductive polymeric material.

25. The apparatus of claim 22, wherein the substrate comprises a non-conductive material selected from the group consisting of printed wiring board material, FR4, and polyamide.

26. The apparatus of claim 22, wherein dimensions of the apparatus are less than or equal to 2 inches×2.5 inches×0.625 inches thick.

27. A portable sensor apparatus configured for in-situ monitoring of surface and sub-surface faults of a structure, the sensor apparatus comprising:
   a primary planar eddy current coil that has a geometrical shape of one of U-shaped, V-shaped, or C-shaped;
   a secondary planar eddy current coil that has the geometrical shape of the planar eddy current coil;
   a direct digital synthesizer and digital-to-analog converter that generate output signals for provision to the primary planar eddy current coil, wherein the direct digital synthesizer is configured to generate the output signals such that the output signals have a range of frequencies;
   an analog-to-digital converter that receives response signals from the secondary planar eddy current coil and digitizes the response signals to generate input signals, and wherein the response signals are indicative of severity and depth of a flaw in the structure, and wherein said analog-to-digital converter, said digital-to-analog converter, and said direct digital synthesizer are synchronized;
   circuitry for calculating a voltage ratio and phase shift between the input and output signals,
   wherein said circuitry comprises the primary planar eddy current coil and the secondary planar eddy current coil; and
   a battery that provides electrical power to the direct digital synthesizer, the digital-to-analog converter, the analog-to-digital converter, and the circuitry for calculating the voltage ratio and phase shift between the input and output signals.

28. The sensor apparatus of claim 27, wherein the circuitry for calculating the voltage ratio and phase shift between the input and output signals comprises a bridge circuit that is configured to measure a differential impedance change between the primary and secondary planar eddy current coils.

29. The sensor apparatus of claim 27, wherein said circuitry comprises a microcontroller.

30. The sensor apparatus of claim 27, wherein said sensor operates over a range of frequencies from approximately 100 Hz to approximately 100 kHz.

31. The sensor apparatus of claim 27, further comprising a resonant circuit configuration comprising a capacitor in parallel with at least one of the primary eddy current coil or the secondary planar eddy current coil.

32. The sensor apparatus of claim 27, wherein said sensor comprises at least one additional planar eddy current coil.

33. The sensor apparatus of claim 27, wherein the primary planar eddy current coil, the secondary planar eddy current coil, the direct digital synthesizer, the digital-to-analog converter, the analog-to-digital converter, and the circuitry are integrated on a common substrate.

* * * * *